United States Patent
Brodie et al.

(10) Patent No.: US 11,053,476 B2
(45) Date of Patent: Jul. 6, 2021

(54) GENERATION OF CANCER STEM CELLS AND USE THEREOF

(71) Applicant: EXOSTEM BIOTEC LTD., Tel Aviv (IL)

(72) Inventors: Chaya Brodie, Southfield, MI (US); Shlomit Brodie, Nof Ayalon (IL)

(73) Assignee: EXOSTEM BIOTEC LTD., Tel Aviv (IL)

( * ) Notice: Subject to any disclaimer, the term of this patent is extended or adjusted under 35 U.S.C. 154(b) by 255 days.

(21) Appl. No.: 16/079,279

(22) PCT Filed: Feb. 23, 2017

(86) PCT No.: PCT/IL2017/050233
§ 371 (c)(1),
(2) Date: Aug. 23, 2018

(87) PCT Pub. No.: WO2017/145162
PCT Pub. Date: Aug. 31, 2017

(65) Prior Publication Data
US 2019/0194622 A1  Jun. 27, 2019

Related U.S. Application Data

(60) Provisional application No. 62/298,603, filed on Feb. 23, 2016.

(51) Int. Cl.
*C12N 5/095* (2010.01)
*C12N 15/113* (2010.01)
*G01N 33/50* (2006.01)

(52) U.S. Cl.
CPC .......... *C12N 5/0695* (2013.01); *C12N 15/113* (2013.01); *G01N 33/5011* (2013.01); *G01N 33/5073* (2013.01); *C12N 2310/141* (2013.01); *C12N 2501/10* (2013.01); *C12N 2501/11* (2013.01); *C12N 2501/148* (2013.01); *C12N 2501/15* (2013.01); *C12N 2501/21* (2013.01); *C12N 2501/2306* (2013.01); *C12N 2501/999* (2013.01); *C12N 2502/1157* (2013.01); *C12N 2502/1323* (2013.01); *C12N 2502/1352* (2013.01); *C12N 2502/30* (2013.01)

(58) Field of Classification Search
CPC .................................................. C12N 5/0695
See application file for complete search history.

(56) References Cited

U.S. PATENT DOCUMENTS

2014/0186872 A1  7/2014  Feve et al.
2015/0104864 A1  4/2015  Hong et al.

FOREIGN PATENT DOCUMENTS

WO  2014138455 A1  9/2014
WO  2014179559 A1  11/2014

OTHER PUBLICATIONS

Hjelmeland et al. "Acidic stress promotes a glioma stem cell phenotype." Cell Death & Differentiation 18.5 (Mar. 12, 2010): 829-840) (Year: 2010).*
Hjelmeland et al. (Cell Death and Differentiation (2011) 18, 829-840). (Year: 2011).*
Lee et al. (Oncotarget 2013; 4: 346-361) (Year: 2013).*
Yin et al. (Frontiers in Bioscience 19, 818-824, Jan. 1, 2014]). (Year: 2014).*
Fessler E et al, "Endothelial cells induce cancer stem cell features in differentiated glioblastoma cells via bFGF.", Mol Cancer, Aug. 2015, 14:157, pp. 1-12.
Hjelmeland, Anita B., et al., "Acidic stress promotes a glioma stem cell phenotype." Cell Death & Differentiation, Dec. 3, 2010, vol. 18 No. 5, pp. 829-840.
Codrici, Elena, et al., "Glioma stem cells and their microenvironments: providers of challenging therapeutic targets.", Stem cells international, Jan. 6, 2016, pp. 1-20.
Tilson, Samantha G., et al., "ROCK inhibition facilitates in vitro expansion of glioblastoma stem-like cells.", PLOS One, Jul. 13, 2015, vol. 10 No. 7, pp. 1-13.
Shi, Lei, et al., "Hypothermia stimulates glioma stem spheres to spontaneously dedifferentiate adjacent non-stem glioma cells.", Cellular and molecular neurobiology, Mar. 2015, vol. 35 No. 2, pp. 217-230.
Zhang, Xiaoqin, et al., "Long non-coding RNAs dysregulation and function in glioblastoma stem cells.", Non-Coding RNA, Jun. 2015, vol. 1 No. 1, pp. 69-86.
Montana, Vedrana., "Glioma: the Mechanisms of Infiltrative Growth.", Opera Medica et Physiologica, Jan. 16, 2016, vol. 2 No. 1, pp. 69-76.
Lu, Lin, et al., "Cancer stem cell vaccine inhibits metastases of primary tumors and induces humoral immune responses against cancer stem cells.", Oncoimmunology, Jan. 9, 2015, vol. 4 No. 3, pp. 1-35.
Lee, Jeongwu, et al., "Tumor stem cells derived from glioblastomas cultured in bFGF and EGF more closely mirror the phenotype and genotype of primary tumors than do serum-cultured cell lines." Cancer cell, May 13, 2006, vol. 9 No. 5, pp. 391-403.
International Search Report PCT/IL2017/050233 Completed May 22, 2017; dated May 23, 2017 5 pages.
Written Opinion of the International Searching Authority PCT/IL2017/050233 dated May 23, 2017 9 pages.

* cited by examiner

*Primary Examiner* — Scott Long
(74) *Attorney, Agent, or Firm* — The Roy Gross Law Firm, LLC; Roy Gross

(57) ABSTRACT

Methods, kits and compositions for generating cancer stem cells are provided.

20 Claims, 6 Drawing Sheets

GENERATION OF CANCER STEM CELLS AND USE THEREOF

CROSS REFERENCE TO RELATED APPLICATIONS

This application is a National Phase of PCT Patent Application No. PCT/IL2017/050233 having International filing date of Feb. 23, 2017, which claims the benefit of priority to U.S. Provisional Patent Application No. 62/298,603, filed Feb. 23, 2016, The contents of the above applications are all incorporated by reference as if fully set forth herein in their entirety.

FIELD OF INVENTION

The present invention is directed to the field of generating cancer stem cells from differentiated cancer cells.

BACKGROUND OF THE INVENTION

Cancer stem cells (CSCs) represent a subset of tumor cells that have the ability to self-renew, generate the diverse cells that comprise the tumor, and continually sustain tumorigenesis. CSCs share important characteristics with normal tissue stem cells, including self-renewal (by symmetric and asymmetric divisions) and differentiation capacity, albeit in an aberrant mode. The first evidence for the existence of CSCs came from acute myeloid leukemia in which a rare subset comprising 0.01-1% of the total population could induce leukemia when transplanted into immunodeficient mice. CSCs are distinct from the cell of origin, which specifically refers to the cell type that receives the first oncogenic hit(s). Moreover, CSCs do not necessarily originate from the transformation of normal stem cells, but may arise from restricted progenitors or more differentiated cells that have acquired self-renewing capacity.

Glioma stem cells (GSCs) were one of the first CSCs isolated from solid tumors. Glioblastomas (GBMs) contain a small subpopulation of self-renewing and tumorigenic cancer CSCs which are implicated in tumor infiltration, resistance to conventional therapies, and tumor recurrence. Interestingly, GSCs isolated from human tumors and cultured in vitro showed remarkable similarities to normal neural stem cells (NSCs), expressing neural stem/progenitor markers such as Nestin, Sox2, and Olig2 and upon induction, could be differentiated to cells expressing neuronal or glial markers. Transplantation of GSCs into immunodeficient mice yielded tumors that shared similar histology and global gene expression patterns with their parental tumors. Understanding the mechanisms associated with the stemness and oncogenic features of these cells is essential for the development of therapeutic approaches that can eradicate GSCs and may provide the basis for the development of novel therapeutic approaches for GBM patients.

There is an unmet need for in vitro cancer models that can recapitulate in vitro and in vivo many of the characteristics of the parental tumors. Such in vitro physiological models can be applied for the high throughput screening of novel and repurposed drugs, can evaluate target organ toxicity and can be used to study cancer metastasis in a disease model. In addition, such in vitro models can help to reduce the use of animal models in research laboratories and pharmaceutical companies. However, the extraction and purification of CSCs for use in this modeling is difficult and expensive, and for some patients impossible. A method of producing CSC, and specifically CSCs that can recapitulate most if not all aspects of a patient's cancer, is greatly needed.

SUMMARY OF THE INVENTION

The present invention provides methods of generating a cancer stem cell (CSC) from a differentiated cancer cell, as well as methods of use thereof, such as for identifying an anti-cancer therapy, and generating a cancer vaccine.

According to a first aspect, there is provided a method for generating a cancer stem cell (CSC), the method comprising:
a. providing a differentiated cancer cell,
b. incubating the differentiated cancer cell in a first medium with a pH between 5 and 6.5,
c. incubating the differentiated cancer cell in a second medium supplemented with epidermal growth factor (EGF) and fibroblast growth factor (FGF),
thereby generating a CSC.

In some embodiments, the differentiated cancer cell is selected from the group consisting of: a primary tumor cell from a subject, a cell of a cancer cell line, a circulating tumor cell from a subject's blood or lymph and a cancer cell differentiated in culture.

In some embodiments, the first medium has a pH between 5.8 and 6.2. In some embodiments, the incubating in a first medium is performed for 15-120 minutes.

In some embodiments, the second medium is further supplemented with a supplement comprising at least one cytokine selected from the group consisting of: IL-6, TGF-$\beta$, TNF-$\alpha$, CTGF, SPARC, and SDF1. In some embodiments, the second medium is further supplemented with TGF-$\beta$.

In some embodiments, the method further comprises co-incubation with cells selected from the group consisting of: mesenchymal stem cells (MSCs), macrophages, microglia, hematopoietic progenitors, and circulating tumor cells. In some embodiments, the method further comprises co-incubation with cells selected from the group consisting of: amniotic MSCs, adipose MSCS, M2 macrophages, and microglia.

In some embodiments, the MSCs are autologous to said differentiated cancer cell. In some embodiments, the second medium is further supplemented with conditioned media or exosomes from any one of human fibroblasts, amniotic MSCs, adipose MSCs or microglia.

In some embodiments, the second medium is further supplemented with one or more small molecules selected from the group consisting of: a Rho-associated protein kinase (ROCK) inhibitor, a GSK3 inhibitor, a monoamine oxidase (MAO) inhibitor, a protein kinase C (PKC) activator, a histone modifying enzyme inhibitor, and a histone modifying enzyme activator.

In some embodiments, the second medium is further supplemented with one or more small molecules selected from the group consisting of: Y-27632, CHIR99021, tranylcypromine, PMA, 3-deazaneplanocin A, 5-aza-2'-deoxycytidine, 4-phenylbutyrate, PKC alpha, PKC epsilon, valproic acid and insulin. In some embodiments, the second medium is further supplemented with one or more small molecules selected from the group consisting of: Y-27632, CHIR99021, tranylcypromine, PMA, 3-deazaneplanocin A, 5-aza-2'-deoxycytidine, 4-phenylbutyrate, PKC alpha and PKC epsilon.

In some embodiments, the methods of the invention further comprise ectopically expressing within the differentiated cancer cell at least one microRNA (miR) selected from the group consisting of: miR-23a, miR-99b, miR-335, miR-339, miR-541, miR-3133, miR-32, miR-99b, miR-320, miR-182, miR-21, miR-138, miR-29a, miR-494, miR-335, miR-214, miR-199, miR-193, miR-196, miR-487, miR-409, miR-193, miR-379, miR-27, miR-193, miR-23, miR-24, miR-299, miR-431, and miR-154. In some embodiments, the methods of the invention further comprise ectopically expressing within the differentiated cancer cell at least one miR or protein selected from the group consisting of: Lin-28, miR-182, and miR-21.

In some embodiments, the methods of the invention further comprise ectopically expressing within the differentiated cancer cell at least one polynucleotide inhibitor that hybridized to at least one miR selected from the group consisting of: miR-3180, miR-34, miR-139, miR-831, miR-4281, miR-1268, miR-3188, miR-135, miR-1228, miR-3141, miR-1207, miR-638, miR-760, miR-2861, miR-15, miR-933, miR-3155, miR-920, miR-4310, miR-1915, miR-26b, miR-664, miR-718, miR-3176, miR-1825, miR-3180, miR-363, miR-1231, miR-20b, miR-572, miR-504, miR-30a, miR-891, miR-9, miR-874, miR-1287, miR-532, miR-362, miR-181, miR-491, miR-1208, miR-330, miR-374, miR-769, miR-501, miR-128, miR-149, miR-505, miR-660, miR-1275, 20a, miR-106, miR-636, miR-145, miR-124, miR-137. In some embodiments, the methods of the invention further comprise ectopically expressing within the differentiated cancer cell a polynucleotide inhibitor that hybridizes to miR-3180.

In some embodiments, the methods of the invention further comprise ectopically expressing within the differentiated cancer cell at least one long non-coding RNA (lncRNA) selected from the group consisting of: ZEB2NAT, UCA1, Zfhx2as, 7SL, antiPeg11, and H19.

In some embodiments, the methods of the invention further comprise ectopically expressing within the differentiated cancer cell at least one protein selected from the group consisting of: Lin-28, STAT3, NFKB, CEBP/B, SOX2, OCT4, WNT5A, LIF, COX2, RUNX2 and NANOG.

In some embodiments, the methods of the invention further comprise irradiating the differentiated cancer cell.

In some embodiments, the incubating (ii) in a second media further comprises incubating in a hypoxic condition. In some embodiments, the hypoxic condition is 2-4% oxygen.

In some embodiments, the methods of the invention further comprise incubating the differentiated cancer cell on adherent or non-adherent plates and selecting primary spheroids. In some embodiments, the methods of the invention further comprise re-plating cells from the spheroids in limiting dilution to form secondary spheroids.

In some embodiments, the methods of the invention are for maintaining the CSC, and further comprise culturing the generated CSC with healthy cells, their exosomes, or a combination thereof. In some embodiments, the healthy cells are from the same tissue of origin as said differentiated cancer cell.

In some embodiments, the methods of the invention further comprise analyzing expressed and secreted markers of the generated CSC.

According to another aspect, there is provided a method for identifying an anti-cancer therapy, the method comprising:
 a. providing CSCs generated by any one of the methods of the invention,
 b. applying a therapy of interest (e.g., a therapeutic agent) to the CSCs,
 c. determining at least one effect of the therapy of interest on the CSCs,
thereby identifying an anti-cancer therapy.

In some embodiments, the effect is a negative effect on the survival or metastatic potential of the CSCs. In some embodiments, the CSCs express a stem cell reporter gene. In some embodiments, the effect is a negative effect on the expression of said reporter gene.

In some embodiments, the methods of the invention further comprise administering the CSCs to a immunodeficient mouse to generate a xenograft before applying the therapy.

In some embodiments, the methods of the invention are for identifying a secondary cancer therapy, wherein the CSCs are resistant to a primary cancer therapy.

In some embodiments, the methods of the invention are for providing a personalized cancer therapy to a subject in need thereof, wherein the CSCs are generated from a differentiated cancer cell from the subject or from cells with the same or similar mutations as the cancer of the subject. In some embodiments, the cancer cell from the subject is a primary tumor cell or a circulating tumor cell from the subject's blood, CSF or other bodily fluid.

In some embodiments, the methods of the invention further comprise analyzing expressed and secreted markers of the CSCs after application of the therapy.

In some embodiments, the methods of the invention further comprise proscribing to the subject the therapy of interest as a personalized cancer therapy. In some embodiments, the methods of the invention further comprise treating the subject by administering the therapy of interest to the subject. In some embodiments, the subject has yet to have a relapse following primary cancer treatment or has had a relapse following primary cancer treatment. In some embodiments, the subject has had metastases of the cancer.

According to another aspect, there is provided a method for producing a cancer vaccine, the method comprising:
 a. generating CSCs by any of the methods of the invention,
 b. incubating dendritic cells with at least one of lysates, exosomes or extracellular vesicles from the CSCs,
 c. harvesting the dendritic cells,
thereby producing a cancer vaccine.

In some embodiments, the dendritic cells are autologous or allogenic to a subject in need of said cancer vaccine. In some embodiments, the methods of the invention further comprise administering a composition comprising the cancer vaccine and a pharmaceutically acceptable carrier or excipient to a subject in need of a cancer vaccine.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

DETAILED DESCRIPTION OF THE INVENTION

Figure 1:
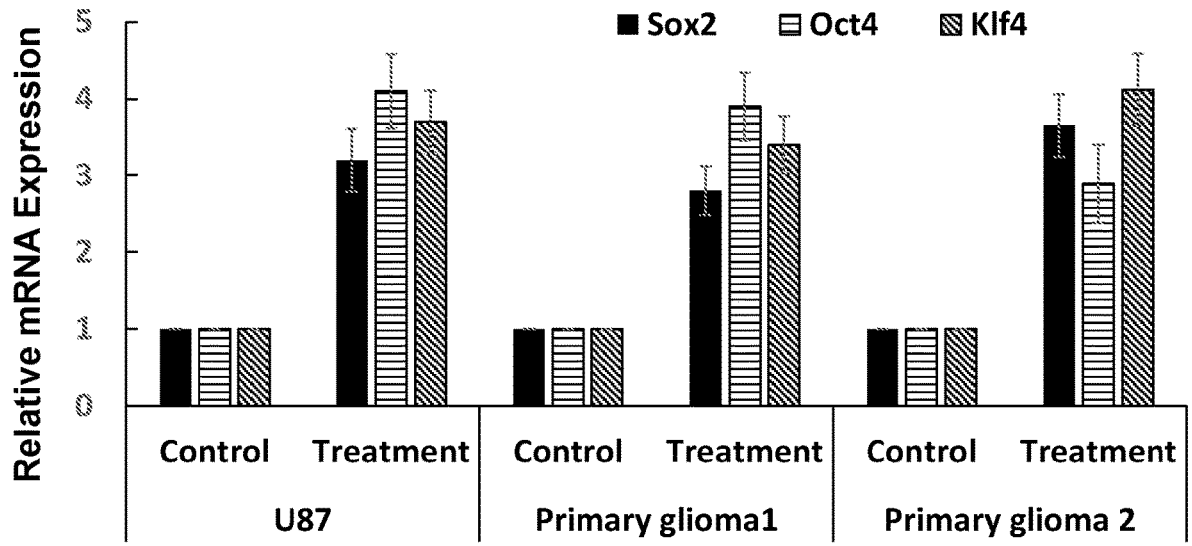
FIG. 1 is a bar graph of relative mRNA expression of stemness markers in U87 cells and primary glioma cells.

The present invention provides, in some embodiments, a method for generating a cancer stem cell (CSC) from a differentiated cancer cell. The invention further provides, in some embodiments a method for identifying an anti-cancer therapy, comprising generating cancer stem cells according to the methods of the invention, applying a therapy of interest to the CSCs and determining at least one effect of the therapy on the CSCs.

Methods of Generating CSCs

By one aspect, the present invention concerns a method for generating a CSC, the method comprising: providing a differentiated cancer cell, incubating the differentiated cancer cell in a first medium with a pH between 5 and 6.5, and incubating the differentiated cancer cell in a second medium supplemented with epidermal growth factor (EGF) and fibroblast growth factor (FGF), thereby generating a CSC.

CSCs can be identified by a number of markers well known to one skilled in the art. These include, but are not limited to: fluorescent-based substrates such as BODIPY aminoacetaldehyde (Aldefluor substrate) for isolation of cells with intracellular ALDH activity (ALDHbright cells); side population (SP) analysis which is based on the efflux of Hoechst 33342 fluorescent dye, reduced 26S proteasome activity, or surface marker identification by FACS.

Non-limiting examples of markers for CSCs include:
Gliomas: Nestin, CD133, CD44
Breast tumors: CD24−/low, CD44+, ALDHbright, CD133, CD221
Colon Cancer: CD133+, CD44+, CD24+, CD166+, Lgr5+, ALDHbright
Liver cancer: CD133+, CD90+, EpCAM+/CD44+, CD13+, SP
Lung and Lung mets: CD44+, CD133+, CD117+, CD87+, SP, ALDHbright
Ovarian: SP, CD133+, CD44+, CD24+, CD117+, EpCAM+, ALDHbright
Pancreatic: CD44+/CD24+/ESA+, CD133+, c-Met+, ALDHbright
Prostate Cancer: CD44+CD24−, CD44+/CD133+/α2β1high, CD44+/CD133+/ABCG2+/CD24−, PSA−/low/ALDHbright/CD44+/α2β1+
Head and neck cancer: CD133+, CD44+, ALDHbright, SP, GRP78+, c-Met+

The terms "differentiation" and "differentiated" as used herein refers to the cellular development of a cell from a primitive stage to a mature formation that is associated inter alia with the expression of characteristic set of cell surface antigenic markers. In the context of cell ontogeny, the adjective "differentiated", or "differentiating" is a relative term. A "differentiated cell" is a cell that has progressed further down the developmental pathway than the cell it is being compared with. Differentiation is a developmental process whereby cells assume a specialized phenotype, e.g., acquire one or more characteristics or functions distinct from other cell types. As used herein, a "differentiated cancer cell" refers to a cancerous cell that is not a cancer stem cell. Such a cell cannot reproduce all the cells of a tumor, nor does it express a plurality of the stem cell markers (e.g., markers listed herein).

In some embodiments, a differentiated cancer cell is selected from the group consisting of: a primary tumor cell from a subject, a cell of a cancer cell line, a circulating tumor cell from a subject's blood or lymph and a cancer cell differentiated in culture. In some embodiments, the differentiated cancer cell is derived or obtained from a subject. In some embodiments, the differentiated cancer cell is a cell of a cell line. In some embodiment, the differentiated cancer cell is a circulating tumor cell.

The term "circulating tumor cells", as used herein, refers to cancer cells that have detached from a primary tumor and travel through the bloodstream or lymphatic system. Methods of extracting circulating tumor cells are well known in the art, and kits for performing such an extraction can be purchased from CELLSEARCH for example.

In some embodiments, the method of generating CSCs is in case tumor specimens are not available or in case CSCs cannot directly be gathered from an available tumor specimen. In some embodiments, the method generates CSCs that recapitulate the characteristics of cancer stem cells and genetic aberrations of the parental tumors, of primary cultures, and of cell lines that carry specific mutations.

In some embodiments, there is provided a method for generating "on the shelf" CSC cells from different tumors and with optionally with different mutations.

In some embodiments, the method of the invention comprises a first incubation of the differentiated cancer cell in an acidic first medium. In some embodiments, the first medium has a pH between 4.6-6.5, 4.8-6.5, 5.0-6.5, 5.2-6.5, 5.4-6.5, 5.6-6.5, 5.8-6.5, 6.0-6.5, 4.6-6.4, 4.8-6.4, 5.0-6.4, 5.2-6.4, 5.4-6.4, 5.6-6.4, 5.8-6.4, 6.0-6.4, 4.6-6.3, 4.8-6.3, 5.0-6.3, 5.2-6.3, 5.4-6.3, 5.6-6.3, 5.8-6.3, 6.0-6.3, 4.6-6.2, 4.8-6.2, 5.0-6.2, 5.2-6.2, 5.4-6.2, 5.6-6.2, 5.8-6.2, 6.0-6.2, 4.6-6.1, 4.8-6.1. 5.0-6.1, 5.2-6.1, 5.4-6.1, 5.6-6.1, 5.8-6.1, 4.6-6.0, 4.8-6.0, 5.0-6.0, 5.2-6.0, 5.4-6.0, 5.6-6.0, or 5.8-6.0. Each possibility represents a separate embodiment of the current invention.

In some embodiments, the method comprises incubating said differentiated cancer cell in a first medium with a pH between 5 and 6.5. In some embodiments, the method comprises incubating said differentiated cancer cell in a first medium with a pH between 5.8 and 6.2.

In some embodiments, the incubating in a first medium is performed for any one of 10-180, 10-150, 10-120, 10-90, 10-60, 15-180, 15-150, 15-120, 15-90, 15-60, 20-180, 20-150, 20-120, 20-90, 20-60, 25-180, 25-150, 25-120, 25-90, 25-60, 30-180, 30-150, 30-120, 30-90, or 30-60, minutes. Each possibility represents a separate embodiment of the current invention. In some embodiments, the incubating in a first medium is performed for 15-120 minutes.

Media used for the incubation of cancer cells and cancer stem cells will be well known to one skilled in the art. Non-limiting examples include, DMEM, RPMI, F12, IMDM, and MEM. In some embodiments, anyone of the incubation media of the methods provided herein has low glucose. In some embodiments, the media of incubation one or two or both has less than 5 g/L, 4 g/L, 3 g/L, 2 g/L, 1 g/L, or 0.5 g/L glucose. Each possibility represents a separate embodiment of the current invention.

In some embodiments, the second medium is supplanted with EGF at a concentration of at least 1, 2, 5, 7, 10, 12, or 15 ng/nl. In some embodiments, the second medium is supplanted with EGF at a concentration of at most, 5, 7, 10, 12, 15, 20, or 25 ng/nl. In some embodiments, the second medium is supplanted with EGF at a concentration of between 1-20, 2-20, 5-20, 7-20, 10-20, 12-20, 1-15, 2-15, 5-15, 7-15, 10-15, 12-15, 1-12, 2-12, 5-12, 7-12, or 10-12, ng/nl. In some embodiments, the second medium is supplanted with EGF at a concentration of between 5-20 ng/nl.

In some embodiments, the second medium is supplanted with FGF at a concentration of at least 1, 2, 5, 7, 10, 12, or 15 ng/nl. In some embodiments, the second medium is supplanted with FGF at a concentration of at most, 5, 7, 10, 12, 15, 20, or 25 ng/nl. In some embodiments, the second medium is supplanted with FGF at a concentration of between 1-20, 2-20, 5-20, 7-20, 10-20, 12-20, 1-15, 2-15, 5-15, 7-15, 10-15, 12-15, 1-12, 2-12, 5-12, 7-12, or 10-12, ng/nl. In some embodiments, the second medium is supplanted with FGF at a concentration of between 5-20 ng/nl.

In some embodiments, the incubating in a second medium is performed for 10-180, 10-150, 10-120, 10-90, 10-60, 15-180, 15-150, 15-120, 15-90, 15-60, 20-180, 20-150, 20-120, 20-90, 20-60, 25-180, 25-150, 25-120, 25-90, 25-60, 30-180, 30-150, 30-120, 30-90, or 30-60, minutes. Each possibility represents a separate embodiment of the current invention.

In some embodiments, the incubating in a second media further comprises incubating in a hypoxic condition. In some embodiments, the hypoxic condition is at or below 4.5%, 4%, 3.5%, 3%, or 2.5% oxygen. Each possibility represents a separate embodiment of the current invention. In some embodiments, the hypoxic condition is at or below 3% oxygen.

In some embodiments, the hypoxic condition is 1-4.5%, 1-4%, 1-3.5%, 1-3%, 1.5-4.5%, 1.5-4%, 1.5-3.5%, 1.5-3%, 2-4.5%, 2-4%, 2-3.5%, 2-3%, 2.5-4.5%, 2.5-4%, 2.5-3.5%, or 2.5-3% oxygen. Each possibility represents a separate embodiment of the current invention. In some embodiments, the hypoxic condition is 2-4% oxygen.

Incubating in hypoxia or a hypoxic condition will be well known to a skilled artisan. Special hypoxic incubator chambers can be used for this purpose and are sold by purveyors of tissue culture chamber.

In some embodiments, the methods of the invention further comprise incubating the differentiated cancer cell on adherent or non-adherent plates and selecting primary spheroids. Such spheroids are also known as tumorspheres. Differentiated cancer cells will tend to adhere to adherent plates, thus cells that do not adhere and instead form spheres are CSCs. In some embodiments, the method further comprises re-plating cells from the spheroids in limiting dilution to form secondary spheroids.

Adherent and non-adherent plates will be well known to one skilled in the art. Adherent plates are frequently coated to increase adherence, or made of plastics with high cellular adherence. Examples of such plates include, but are not limited to, classic tissue culture plates such as are sold by Fischer Scientific, Corning, Sigma Aldrich and others, gelatin-coated plates, and collagen coated plates. Non-adherent plates also refer to low-adherence plates such as are common for culturing spheroids.

The term "limiting dilution" as used herein refers to diluting the concentration of cells in a media such that there is a high probability that only a single cell will be present in each sample. In some embodiments, limiting dilution refers to diluting cells such that when plated into wells of a dish there is only one cell in every other well, every third well, every fifth well, or every tenth well. Each possibility represents a separate embodiment of the current invention.

In some embodiments, the methods of the invention further comprise irradiating the differentiated cancer cell. Cell irradiation is well known to one skilled in the art. In some embodiments, the dose of irradiation is at least 1, 5, 10, 15, 20, 30, 40, or 50 grays (gy). Each possibility represents a separate embodiment of the current invention. In some embodiments, the irradiation is a single dose of irradiation. In some embodiments, the irradiation is administered in multiple doses over a period of time not more than a week, not more than 5 days, not more than 3 days, not more than 1 day. Each possibility represents a separate embodiment of the current invention. In some embodiments, the radiation is non-ionizing radiation. In some embodiments, the radiation is ionizing radiation. In some embodiments, the radiation is gamma irradiation.

Supplements

In some embodiments, the second medium is further supplemented with a supplement comprising at least one cytokine. In some embodiments, the cytokine is selected from the group consisting of: pro-inflammatory cytokines, chemokines, and pro-fibrotic cytokines. In some embodiments, the at least one cytokine is selected from the group consisting of: IL-6, TGF-β, TNF-α, CTGF, SPARC, and SDF1.

In some embodiments, the cytokine is supplemented at a concentration of 0.1-100, 0.1-90, 0.1-80, 0.1-70, 0.1-60, 0.1-50, 0.1-40, 0.1-30, 0.1-20, 0.1-10, 1-100, 1-90, 1-80, 1-70, 1-60, 1-50, 1-40, 1-30, 1-20, 1-10, 10-100, 10-90, 10-80, 10-70, 10-60, 10-50, 15-100, 15-90, 15-80, 15-70, 15-60, 15-50, 20-100, 20-90, 20-80, 20-70, 20-60, 20-50, 25-100, 25-90, 25-80, 25-70, 25-60, or 25-50, ng/ml. Each possibility represents a separate embodiment of the current invention. In some embodiments, TNF-α is supplemented at a concentration of 25-80 ng/ml. In some embodiments, IL-6 is supplemented at a concentration of 10-50 ng/ml. In some embodiments, SPARC is supplemented at a concentration of 10-50 ng/ml. In some embodiments, CTGF is supplemented at a concentration of 1-50 ng/ml. In some embodiments, SDF1 is supplemented at a concentration of 1-50 ng/ml. In some embodiments, the second medium is further supplemented with TGF-β. In some embodiments, TGF-β is supplemented at a concentration of 0.1-30 ng/ml.

In some embodiments, the second medium is further supplemented with a supplement comprising at least one small molecule selected from the group consisting of: a Rho-associated protein kinase (ROCK) inhibitor, a GSK3 inhibitor, a sonic hedgehog (SHH) inhibitor, an ERK activator, a monoamine oxidase (MAO) inhibitor, a protein kinase C (PKC) activator, a histone modifying enzyme inhibitor, and a histone modifying enzyme activator.

In some embodiments, inhibitors reduce expression or function of a protein or complex by at least 10, 20, 30, 40, 50, 60, 70, 80, 90, 95, or 99%. Each possibility represents a separate embodiment of the current invention. A person skilled in the art will understand that each small molecule will be administered to cells at a concentration that is specific to that molecule and which is sufficient to cause inhibition. The manufacturer's guidelines should be followed when supplementing with these molecules unless otherwise specified herein below.

In some embodiments, activators increase expression or function of a protein or complex by at least 10, 20, 30, 40, 50, 60, 70, 80, 90, 95, or 99%. Each possibility represents a separate embodiment of the current invention. A person skilled in the art will understand that each small molecule will be administered to cells at a concentration that is specific to that molecule and which is sufficient to cause activation. The manufacturer's guidelines should be followed when supplementing with these molecules unless otherwise specified herein below.

ROCK inhibitors, inhibit Rho-associated protein kinases and are well known in the art. Non-limiting examples include Y-27632, thiazovivin, fasudil, and GSK429286A. GSK inhibitors inhibit glycogen synthase kinase 3A, 3B, and 3C, and are well known in the art. Non-limiting examples include CHIR99021, kenpaullone, SB-216763, indirubin, hymenidin, aloinin A, and lithium chloride. MAO inhibitors inhibit monoamine oxidase A and B and are well known in the art. Non-limiting examples include tranylcypromine, 2-propynal, clorgyline hydrocholoride, ethyl homovanillate, phenelzine sulfate salt, rasagiline, and pimprinine.

Protein kinase C (PKC) alpha, and epsilon are signaling molecules that make up the PKC signaling complex and activators of the complex are well known in the art. Non-limiting examples include, PKCα, PKC epsilon, phorbol 12-myristate 13-acetate (PMA), alpha-amyloid precursor protein, phorbol-12, 13-dibutyrate, mezerein, ingenol 3-angelate, and phorbol 12, 13-dihexanoate. ERK activation is also known to activate PKC. In some embodiments, the ERK activator is Ceramide C6.

Histone modifying enzymes include, but are not limited to, histone acetyltransferases, histone deacetylases, histone methyltransferases, histone demethylases, histone phosphorylases, histone ubiquitinases, histone sumoylases, histone ADP ribosylases, and histone deiminases. Inhibitors and activators of these enzymes are well known in the art and include but are not limited to: 3-deazaneplanocin A, 5-aza-2'-deoxycytidine, 4-phenylbutyrate, TC-H 106, valproic acid, insulin, and SIRT1 activator 3.

In some embodiments, the second medium is further supplemented with a small molecule selected from the group consisting of: Y-27632, CHIR99021, tranylcypromine, PMA, 3-deazaneplanocin A, 5-aza-2'-deoxycytidine, 4-phenylbutyrate, PKC alpha, PKC epsilon, valproic acid and insulin. In some embodiments, the second medium is further supplemented with a small molecule selected from the group consisting of: Y-27632, CHIR99021, tranylcypromine, PMA, 3-deazaneplanocin A, 5-aza-2'-deoxycytidine, 4-phenylbutyrate, PKC alpha and PKC epsilon activators or overexpression.

In some embodiments, the small molecule is supplemented at a concentration of 0.1-100, 0.1-90, 0.1-80, 0.1-70, 0.1-60, 0.1-50, 0.1-40, 0.1-30, 0.1-20, 0.1-10, 1-100, 1-90, 1-80, 1-70, 1-60, 1-50, 1-40, 1-30, 1-20, 1-10, 10-100, 10-90, 10-80, 10-70, 10-60, 10-50, 15-100, 15-90, 15-80, 15-70, 15-60, 15-50, 20-100, 20-90, 20-80, 20-70, 20-60, 20-50, 25-100, 25-90, 25-80, 25-70, 25-60, or 25-50 nm. In some embodiments, PMA is supplemented at a concentration of 1-50 nm.

In some embodiments, the small molecule is supplemented at a concentration of 0.1-100, 0.1-90, 0.1-80, 0.1-70, 0.1-60, 0.1-50, 0.1-40, 0.1-30, 0.1-20, 0.1-10, 1-100, 1-90, 1-80, 1-70, 1-60, 1-50, 1-40, 1-30, 1-20, 1-10, 10-100, 10-90, 10-80, 10-70, 10-60, 10-50, 15-100, 15-90, 15-80, 15-70, 15-60, 15-50, 20-100, 20-90, 20-80, 20-70, 20-60, 20-50, 25-100, 25-90, 25-80, 25-70, 25-60, or 25-50, ng/ml.

Co-Culture

In some embodiments, the second incubation further comprises co-incubation with cells selected from the group consisting of: mesenchymal stem cells (MSCs), macrophages, microglia, hematopoietic progenitors, circulating tumor cells and circulating MSCs from the patient serum or extracted from the patient tumors. In some embodiments, the second incubating further comprises co-incubation with cells selected from the group consisting of: amniotic MSCs, adipose MSCs, M2 macrophages, and microglia.

As used herein, the term "mesenchymal stem cell" or "MSC" refers to a cell capable of giving rise to differentiated cells in multiple mesenchymal lineages, specifically to osteoblasts, adipocytes, myoblasts and chondroblasts. Generally, mesenchymal stem cells also have one or more of the following properties: an ability to undergo asynchronous, or symmetric replication that is where the two daughter cells after division can have different phenotypes; extensive self-renewal capacity; and clonal regeneration of the tissue in which they exist, for example, the non-hematopoietic cells of bone marrow. MSCs can originate in several tissues, including bone marrow, adipose tissue, amnion and chorion of the placenta, dental pulp and umbilical cord. In some embodiments, the MSCs are autologous to the differentiated cancer cell. In some embodiments, the MSCs are allogenic to the differentiated cancer cell.

Hematopoietic progenitors are characterized by expression of CD34 on the cell surface. Such cells can be extracted from circulating blood. They have the capacity to differentiated into any cell of the hematopoietic lineage. In some embodiments, the hematopoietic progenitors are autologous to the differentiated cancer cell. In some embodiments, the hematopoietic progenitors are allogenic to the differentiated cancer cell.

As used herein "M2 macrophages" refer to anti-inflammatory macrophages that decrease local inflammation by release of cytokines and other factors (such as ornithine) and encourage tissue repair. In some embodiments, M2 macrophages are tumor associated macrophages. In some embodiments, the macrophages are autologous to the differentiated cancer cell. In some embodiments, the macrophages are allogenic to the differentiated cancer cell.

In some embodiments, the microglia are co-cultured with a differentiated cancer cell from a brain tumor. In some embodiments, the microglia are autologous to the differentiated cancer cell. In some embodiments, the microglia are allogenic to the differentiated cancer cell.

The co-cultured cells described herein are all known to secrete paracrine factors. In some embodiments, the second medium is further supplemented with conditioned media or exosomes from the above described cells. In some embodiments, the second medium is further supplemented with conditioned media or exosomes from human fibroblasts, amniotic MSCs, adipose MSCs or microglia.

The term "conditioned media" as used herein, refers to media in which cells were already grown for a period of time. This media will have secreted factors, including but not limited to, enzymes, growth factors, cytokines and hormone dissolved in it, which can then be transferred by moving the conditioned media to new cells. One skilled in the art will be familiar with producing conditioned media, and the incubation time in order to condition the media can range from 1-5 days depending on the type of cells growing in the media and their concentration within the media.

As used herein, the term "exosomes" refers to small extracellular vesicles of endocytic origin with a size of 50-100 nm. Exosomes can contain microRNAs (miRNA), long non-coding RNAs (lncRNA), mRNAs, DNA fragments, and proteins, which are shuttled from donor to recipient cells. Exosomes appear to play an important role in the exchange of information in the tumor microenvironment, as they have been shown to mediate transfer of oncogenic proteins between cancer cells. On the other hand, exosomes have also been shown to program the immune system to elicit an anti-tumor response.

Ectopic RNA and Protein Expression

In some embodiments, the methods of the invention further comprise ectopically expressing within the differentiated cancer cell at least one microRNA (miR) selected from the group consisting of miR-23a, miR-99b, miR-335, miR-339, miR-541, miR-3133, miR-32, miR-99b, miR-320, miR-182, miR-21, miR-138, miR-29a, miR-494, miR-335, miR-214, miR-199, miR-193, miR-196, miR-487, miR-409, miR-193, miR-379, miR-27, miR-193, miR-23, miR-24, miR-299, miR-431, and miR-154 and/or Lin-28.

As used herein, the terms "microRNA" or "miR" refer to small non-coding RNA molecule, that contains 18-25 nucleotide (usually between 20-23, and most commonly 22), that binds to at least one mRNA target and inhibits protein expression from that mRNA. miRs are well known to one skilled in the art, and frequently target many mRNAs although not all targets of specific miRs are yet known. In some embodiments, the miR reduces protein produced by an mRNA by at least 20%, 25%, 30%, 35%, 40%, 45%, 50%, 55%, 60%, 65%, 70%, 75%, 80%, 85%, 90%, 95%, or 99%. Each possibility represents a different embodiment of the invention.

The terms "expression" or "expressing" as used herein, refer to the biosynthesis of a gene product or non-coding RNA, including the transcription and/or translation of said gene product or non-coding RNA. Thus, expression of a nucleic acid molecule may refer to transcription of the nucleic acid fragment (e.g., transcription resulting in mRNA or other functional RNA) and/or translation of RNA into a precursor or mature protein (polypeptide).

Expressing of a gene or nucleic acid within a cell is well known to one skilled in the art. It can be carried out by, among many methods, transfection, viral infection, or direct alteration of the cell's genome. In some embodiments, the gene or RNA is in an expression vector such as plasmid or viral vector.

In some embodiments, the RNA molecule (i.e. the miR) is transfected, nucleofected or otherwise transferred directly into the cell, without being in a vector. In some embodiments, the miR is single stranded. In some embodiments, the miR is an RNA duplex. In some embodiments, the miR is in a vector.

A vector nucleic acid sequence generally contains at least an origin of replication for propagation in a cell and optionally additional elements, such as a heterologous polynucleotide sequence, expression control element (e.g., a promoter, enhancer), selectable marker (e.g., antibiotic resistance), poly-Adenine sequence.

The vector may be a DNA plasmid delivered via non-viral methods or via viral methods. The viral vector may be a retroviral vector, a herpesviral vector, an adenoviral vector, an adeno-associated viral vector or a poxviral vector. The promoters may be active in mammalian cells. The promoters may be a viral promoter.

In some embodiments, the gene is operably linked to a promoter. The term "operably linked" is intended to mean that the nucleotide sequence of interest is linked to the regulatory element or elements in a manner that allows for expression of the nucleotide sequence (e.g. in an in vitro transcription/translation system or in a host cell when the vector is introduced into the host cell).

In some embodiments, the vector is introduced into the cell by standard methods including electroporation (e.g., as described in From et al., Proc. Natl. Acad. Sci. USA 82, 5824 (1985)), heat shock, infection by viral vectors, high velocity ballistic penetration by small particles with the nucleic acid either within the matrix of small beads or particles, or on the surface (Klein et al., Nature 327. 70-73 (1987)), and/or the like.

The term "promoter" as used herein refers to a group of transcriptional control modules that are clustered around the initiation site for an RNA polymerase i.e., RNA polymerase II. Promoters are composed of discrete functional modules, each consisting of approximately 7-20 bp of DNA, and containing one or more recognition sites for transcriptional activator or repressor proteins.

In some embodiments, nucleic acid sequences are transcribed by RNA polymerase II (RNAP II and Pol II). RNAP II is an enzyme found in eukaryotic cells. It catalyzes the transcription of DNA to synthesize precursors of mRNA and most snRNA and microRNA.

In some embodiments, mammalian expression vectors include, but are not limited to, pcDNA3, pcDNA3.1(±), pGL3, pZeoSV2(±), pSecTag2, pDisplay, pEF/myc/cyto, pCMV/myc/cyto, pCR3.1, pSinRep5, DH26S, DHBB, pNMT1, pNMT41, pNMT81, which are available from Invitrogen, pCI which is available from Promega, pMbac, pPbac, pBK-RSV and pBK-CMV which are available from Strategene, pTRES which is available from Clontech, and their derivatives.

In some embodiments, expression vectors containing regulatory elements from eukaryotic viruses such as retroviruses are used by the present invention. SV40 vectors include pSVT7 and pMT2. In some embodiments, vectors derived from bovine papilloma virus include pBV-1MTHA, and vectors derived from Epstein Bar virus include pHEBO, and p2O5. Other exemplary vectors include pMSG, pAV009/A+, pMTO10/A+, pMAMneo-5, baculovirus pDSVE, and any other vector allowing expression of proteins under the direction of the SV-40 early promoter, SV-40 later promoter, metallothionein promoter, murine mammary tumor virus promoter, Rous sarcoma virus promoter, polyhedrin promoter, or other promoters shown effective for expression in eukaryotic cells.

In some embodiments, recombinant viral vectors, which offer advantages such as lateral infection and targeting specificity, are used for in vivo expression. In one embodiment, lateral infection is inherent in the life cycle of, for example, retrovirus and is the process by which a single infected cell produces many progeny virions that bud off and infect neighboring cells. In one embodiment, the result is that a large area becomes rapidly infected, most of which was not initially infected by the original viral particles. In one embodiment, viral vectors are produced that are unable to spread laterally. In one embodiment, this characteristic can be useful if the desired purpose is to introduce a specified gene into only a localized number of targeted cells.

Various methods can be used to introduce the expression vector of the present invention into cells. Such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et at. [Biotechniques 4 (6): 504-512, 1986] and include, for example, stable or transient transfection, lipofection, electroporation and infection with recombinant viral vectors. In addition, see U.S. Pat. Nos. 5,464,764 and 5,487,992 for positive-negative selection methods.

In one embodiment, plant expression vectors are used. In one embodiment, the expression of a polypeptide coding sequence is driven by a number of promoters. In some embodiments, viral promoters such as the 35S RNA and 19S RNA promoters of CaMV [Brisson et al., Nature 310:511-514 (1984)], or the coat protein promoter to TMV [Takamatsu et al., EMBO J. 6:307-311 (1987)] are used. In another embodiment, plant promoters are used such as, for example, the small subunit of RUBISCO [Coruzzi et al., EMBO J. 3:1671-1680 (1984); and Brogli et al., Science 224:838-843 (1984)] or heat shock promoters, e.g., soybean hsp17.5-E or hsp17.3-B [Gurley et al., Mol. Cell. Biol. 6:559-565 (1986)]. In one embodiment, constructs are introduced into plant cells using Ti plasmid, Ri plasmid, plant viral vectors, direct DNA transformation, microinjection, electroporation and other techniques well known to the skilled artisan. See, for example, Weissbach & Weissbach [Methods for Plant Molecular Biology, Academic Press, NY, Section VIII, pp 421-463 (1988)]. Other expression systems such as insects and mammalian host cell systems, which are well known in the art, can also be used by the present invention.

It will be appreciated that other than containing the necessary elements for the transcription and translation of the inserted coding sequence (encoding the polypeptide), the expression construct of the present invention can also include sequences engineered to optimize stability, production, purification, yield or activity of the expressed polypeptide.

A person with skill in the art will appreciate that a gene can also be expressed from a nucleic acid construct administered to an individual employing any suitable mode of administration, described hereinabove (i.e., in vivo gene therapy). In one embodiment, the nucleic acid construct is introduced into a suitable cell via an appropriate gene delivery vehicle/method (transfection, transduction, homologous recombination, etc.) and an expression system as needed and then the modified cells are expanded in culture and returned to the individual (i.e., ex vivo gene therapy).

In some embodiments, the methods of the invention further comprise ectopically expressing within the differentiated cancer cell at least one miR or protein selected from the group consisting of: Lin-28, miR-182, and miR-21.

In some embodiments, the methods of the invention further comprise ectopically expressing within the differentiated cancer cell at least one polynucleotide inhibitor that hybridized to at least one miR and inhibits function of the miR, wherein said miR is selected from the group consisting of: miR-139, miR-831, miR-4281, miR-1268, miR-3188, miR-135, miR-1228, miR-3141, miR-1207, miR-638, miR-760, miR-2861, miR-15, miR-933, miR-3155, miR-920, miR-4310, miR-1915, miR-26b, miR-664, miR-718, miR-3176, miR-1825, miR-3180, miR-363, miR-1231, miR-20b, miR-572, miR-504, miR-30a, miR-891, miR-9, miR-874, miR-1287, miR-532, miR-362, miR-181, miR-491, miR-1208, miR-330, miR-374, miR-769, miR-501, miR-128, miR-149, miR-505, miR-660, miR-1275, 20a, miR-106, miR-636, miR-145, miR-124, miR-137.

As used herein, the term "polynucleotide inhibitor" refers to a nucleic acid molecule that hybridizes to and inhibits the function of a miR, i.e. inhibits the miR's ability to reduce protein production by its target mRNAs. Non-limiting examples of polynucleotide inhibitors of miRs include antagomirs, microRNA agomirs, and MISSION synthetic mircroRNA inhibitors. In some embodiments, the polynucleotide inhibitor reduces miR suppression of translation of an mRNA by at least 20%, 25%, 30%, 35%, 40%, 45%, 50%, 55%, 60%, 65%, 70%, 75%, 80%, 85%, 90%, 95%, or 99%. Each possibility represents a different embodiment of the invention. In some embodiments, the methods of the invention further comprise ectopically expressing within the differentiated cancer cell a polynucleotide inhibitor of miR-3180.

In some embodiments, the methods of the invention further comprise ectopically expressing within the differentiated cancer cell a long non-coding RNA (lncRNA) selected from the group consisting of: ZEB2NAT, UCA1, Zfhx2as, 7SL, antiPeg11, and H19.

In some embodiments, the RNA molecule (i.e. the lncRNA) is transfected, nucleofected or otherwise transferred directly into the cell, without being in a vector. In some embodiments, the lncRNA is single stranded. In some embodiments, the lncRNA is an RNA duplex. In some embodiments, the lncRNA is in a vector.

In some embodiments, the methods of the invention further comprise ectopically expressing within said differentiated cancer cell at least one protein selected from the group consisting of: STAT3, NFKB, CEBP/B, SOX2, OCT4, WNT5A, LIF, COX2, RUNX2 and NANOG.

In some embodiments, the methods of the invention further comprise coating the plates of the second incubation with a molecule selected from the group consisting of: SPARC, anti-CD44 antibody, RTVP and RTVP-1b.

Ectopic protein expression is well known to one skilled in the art. In some embodiments, ectopic proteins are added to the media such that the cells of the invention will contact the protein. In some embodiments, the cells of the invention will transport the protein from the media into the cell. In some embodiments, ectopic protein expression comprises ectopic expression of the mRNA that codes for the protein within the cells. In some embodiments, this expression is transient. In some embodiments, the mRNA is stably expressed, such as by integration of DNA into the cells genome. Methods of ectopically expressing a gene within a cell are described herein above.

Methods of Use

In some embodiments, the methods of the invention for maintaining the CSC, further comprise culturing the generated CSC with healthy cells, their exosomes, or a combination thereof. In some embodiments, the methods of the invention for use in maintaining the CSC, further comprise culturing the generated CSC with healthy cells, their exosomes, or a combination thereof. As used herein, "healthy cells" refers to non-cancerous cells. In some embodiments, the healthy cells are from the same tissue of origin as the differentiated cancer cell.

In some embodiments, methods of the invention for maintaining the CSC, further comprise culturing the generated CSC with differentiated cancer cells and healthy cells. In some embodiments, methods of the invention for use in maintaining the CSC, further comprise culturing the generated CSC with differentiated cancer cells and healthy cells. Such a combination of CSCs, differentiated cancer cells and healthy cells when 3-dimensional is herein referred to as an organoid. Such organoids are useful as models for testing cancer therapeutics, as they more accurately mimic the in vivo tumor, than any one cell type alone.

In addition to the generation of the cancer stem cells/tumorspheres, the invention also provides a method of growing the generated cells in 3D-spheroid cultures alone or with combination of cells that generate the microenvironment of the tumors. In some embodiments, these other cells are selected from the group consisting of: endothelial cells, stromal, glial, microglial and immune cells, or exosomes or conditioned media from these cells. This allows for the screening of drugs in a more relevant context. In some embodiments, the invention provides for a method of analyzing multiple parameters together in living cells using dual fluorescent luciferase-based reporters that allow analysis of cell fate, cell death, stemness, differentiation, mesenchymal transformation, and activation of signaling pathways altogether.

In some embodiments, the CSCs of the invention are administered to a immunodeficient mouse to generate a xenograft. A cancer xenograft is also a useful model for testing cancer therapeutics, as a fully integrated tumor forms in the mouse.

As used herein, the terms "administering," "administration," and like terms refer to any method which, in sound medical practice, delivers a composition containing an active agent to a subject in such a manner as to provide a therapeutic effect. One aspect of the present subject matter provides for oral administration of a therapeutically effective amount of a composition of the present subject matter to a patient in need thereof. Other suitable routes of administration can include parenteral, subcutaneous, intravenous, intramuscular, or intraperitoneal.

In some embodiments, the methods of the invention further comprise analyzing expressed and secreted markers of the generated CSCs. In some embodiments, the CSCs being analyzed are in culture. In some embodiments, the CSCs being analyzed are in tumorspheres. In some embodiments, the CSCs being analyzed are in organoids. In some embodiments, the CSCs being analyzed are in xenografts.

In some embodiments, the expressed and secreted markers that can be proteins, specific miRNAs, lncRNAs and other non-coding RNAs. In some embodiments, the expressed and secreted markers are isolated from media or exosomes or other extracellular vesicles. In some embodiments, the expressed and secreted markers are employed for the analysis of disease presence and progression and for the response of the cells to specific treatments. In some embodiments, the analysis can be later applied for isolating circulating biomarkers from different body fluids (blood, serum, plasma, urine, CSF, saliva). In some embodiments, this method is a non-invasive procedure to analyze and predict disease progression, relapse and response to treatment.

By another aspect, there is provided a method for identifying an anti-cancer therapy, the method comprising: providing CSCs generated by any of the methods of the invention, applying a therapy of interest to the CSCs, determining at least one effect of the therapy of interested on the CSCs, thereby identifying an anti-cancer therapy.

The term "therapy of interest" as used herein, refers to any therapy or drug that may, or is suspected of, treating or ameliorating cancer. Such a therapy or drug may be a known cancer therapeutic. Such a therapy or drug may only be suspected of being a cancer therapeutic. Such a therapy or drug may be a therapeutic for use in treating a different disease or condition, but may have a secondary therapeutic use in treating cancer.

The therapy of interest or therapeutic agent of interest can include, but is not limited to, gamma radiation, abiraterone acetate, methotrexate, paclitaxel albumin-stabilized nanoparticle formulation, ABVC (doxorubicin hydrochloride, bleomycin, vinblastine sulfate, dacarbazine combination), ABVE (doxorubicin hydrochloride, bleomycin, vinblastine sulfate, etoposide combination), ABVE-PC (doxorubicin hydrochloride, bleomycin, vinblastine sulfate, etoposide, prednisone, cyclophosphamide combination), AC (doxorubicin hydrochloride and cyclophosphamide combination), AC-T (doxorubicin hydrochloride, cyclophosphamide, paclitaxel combination), brentuximab vedotin, ADE (cytarabine, daunorubicin hydrochloride, etoposide combination), ado-trastuzumab emtansine, doxorubicin hydrochloride, fluorouracil, afatinib dimaleate, everolimus, imiquimod, aldesleukin, alemtuzumab, pemetrexed disodium, palonosetron hydrochloride, chlorambucil, aminolevulinic acid, anastrozole, aprepitant, pamidronate disodium, exemestane, nelarabine, arsenic trioxide, ofatumumab, asparaginase *Erwinia chrysanthemi*, bevacizumab, axitinib, azacitidine, BEACOPP (bleomycin, etoposide, doxorubicin hydrochloride, cyclophosphamide, vincristine sulfate, procarbazine hydrochloride, prednisone combination), carmustine, belinostat, bendamustine hydrochloride, BEP (bleomycin, etoposide, cisplatin combination), bevacizumab, bexarotene, tositumomab, I 131 Iodine tositumomab, bicalutamide, carmustine, bleomycin, bortezomib, bosutinib, busulfan, cabazitaxel, cabozantinib-S-malate, CAF (cyclophosphamide, doxorubicin hydrochloride, fluorouracil combination), irinotecan hydrochloride, capecitabine, CAPDX (capecitabine, oxaliplatin combination), carboplatin, carboplatin-taxol combination, carfilzomib, carmustine implant, lomustine, ceritinib, daunorubicin hydrochloride, recombinant HPV bivalent vaccine, cetuximab, chlorambucil, chlorambucil-prednisone combination, CHOP (cyclophosphamide, doxorubicin hydrochloride, vincristine sulfate, prednisone combination), cisplatin, cyclophosphamide, clofarabine, CMF (cyclophosphamide, methotrexate, fluorouracil combination), COPP (cyclophosphamide, vincristine sulfate, procarbazine hydrochloride, prednisone combination), COPP-ABV (cyclophosphamide, vincristine sulfate, procarbazine hydrochloride, prednisone, doxorubicin hydrochloride, bleomycin, vinblastine sulfate combination), dactinomycin, crizotinib, CVP (cyclophosphamide, vincristine sulfate, prednisone combination), ifosfamide, ramucirumab, cytarabine, liposomal cytarabine, dabrafenib, dacarbazine, decitabine, dactinomycin, dasatinib, degarelix, denileukin diftitox, denosumab, dexrazoxane hydrochloride, docetaxel, doxorubicin hydrochloride liposome, fluorouracil, rasburicase, epirubicin hydrochloride, oxaliplatin, eltrombopag olamine, enzalutamide, EPOCH (etoposide, prednisone, vincristine sulfate, cyclophosphamide, doxorubicin hydrochloride combination), eribulin mesylate, vismodegib, erlotinib hydrochloride, etoposide phosphate, etoposide, everolimus, raloxifene hydrochloride, toremifene, fulvestrant, FEC (fluorouracil, epirubicin hydrochloride, cyclophosphamide combination), letrozole, filgrastim, fludarabine phosphate, fluorouracil, FOLFIRI (leucovorin calcium, fluorouracil, irinotecan hydrochloride combination), FOLFIRI-bevacizumab combination, FOLFIRI-cetuximab combination, FOLFIRINOX (leucovorin calcium, fluorouracil, irinotecan hydrochloride, oxaliplatin combination), FOLFOX (leucovorin calcium, fluorouracil, oxaliplatin combination), pralatrexate, FU-LV (fluorouracil, leucovorin calcium combination), recombinant HPV quadrivalent vaccine, obinutuzumab, gefitinib, gemcitabine hydrochloride, gemcitabine-cisplatin combination, gemcitabine-oxaliplatin combination, gemtuzumab ozogamicin, imatinib mesylate, glucarpidase, goserelin acetate, trastuzumab, topotecan hydrochloride, hyper-CVAD (cyclophosphamide, vincristine sulfate, doxorubicin hydrochloride, dexamethasone combination), ibritumomab tiuxetan, ibrutinib, ICE (ifosfamide, carboplatin, etoposide combination), ponatinib hydrochloride, idarubicin hydrochloride, idelalisib, ifosamide, axitinib, recombinant interferon α-2b, ipilimumab, irinotecan hydrochloride, romidepsin, ixabepilone, ruxolitinib phosphate, palifermin, pembrolizumab, lapatinib ditosylate, lenalidomide, letrozole, leucovorin calcium, leuprolide acetate, vincristine sulfate liposome, procarbazine hydrochloride, mechlorethamine hydrochloride, megestrol acetate, trametinib, mercaptopurine, mesna, temozolomide, mitomycin C, mitoxantrone hydrochloride, MOPP (mechlorethamine hydrochloride, vincristine sulfate, procarbazine hydrochloride, prednisone combination), plerixafor, vinorelbine tartrate, nelarabine, sorafenib tosylate, nilotinib, tamoxifen citrate, romiplostim, obinutuzumab, ofatumumab, omacetaxine mepesuccinate, pegaspargase, OEPA (vincristine sulfate, etoposide, prednisone, doxorubicin hydrochloride combination), OFF (oxaliplatin, fluorouracil, leucovorin calcium combination), OPPA (vincristine sulfate, procarbazine hydrochloride, prednisone, doxorubicin hydrochloride combination), paclitaxel, PAD (bortezomib, doxorubicin hydrochloride, dexamethasone combination), palifermin, palonosetron hydrochloride, pamidronate disodium, panitumumab, pazopanib hydrochloride, peginterferon α-2b, pembrolizumab, pemetrexed disodium, pertuzumab, plerixafor, pomalidomide, ponatinib hydrochloride, pralatrexate, prednisone, procarbazine hydrochloride, sipuleucel-T, radium 223 dichloride, R-CHOP (rituximab, cyclophosphamide, doxorubicin hydrochloride, vincristine sulfate, prednisone combination), R-CVP (rituximab, cyclophosphamide, vincristine sulfate, prednisone combination), reforafenib, rituximab, romidepsin, ruxolitinib phosphate, talc, siltuximab, sipuleucel-T, sorafenib tosylate, STANFORD V (mechlorethamine hydrochloride, doxorubicin hydrochloride, vinblastine sulfate, vincristine sulfate, bleomycin, etoposide, prednisone combination), sunitinib malate, thalidomide, TAC (docetaxel, doxorubicin hydrochloride, cyclophosphamide combination), temozolomide, temsirolimus, topotecan hydrochloride, toremifene, TPF (docetaxel, cisplatin, fluorouracil combination), trametinib, trastuzumab, vandetanib, VAMP (vincristine sulfate, doxorubicin hydrochloride, methotrexate, prednisone combination), VeIP (vinblastine sulfate, ifosamide, cisplatin combination), vinblastine sulfate, vemurafenib, vincristine sulfate, vincristine sulfate liposome, vinorelbine tartrate, VIP (etoposide, ifosfamide, cisplatin combination), vismodegib, vorinostat, XELOX (capecitabine, oxaliplatin combination), ziv-aflibercept, zoledronic acid, or combinations thereof.

In some embodiments, the therapy of interest also comprises any suitable gene therapeutics, such as, but not limited to, adeno-associated viruses and adenoviruses, lentiviruses, or any other viral vectors as known in the art that can modulate gene expression. The therapy of interest can further include, but is not limited to, small molecules, peptides, repurposed drugs, oncogene siRNAs, overexpression of tumor suppressors, overexpressing or silencing specific lncRNAs, allele specific siRNA for a mutant protein, miRNAs, antagomiRs, polynucleotide inhibitors that bind to miRs, oncolytic viruses, or cell-based therapy using prodrugs.

In some embodiments, the at least one effect of the therapy of interest is a negative effect on the survival or metastatic potential of the CSCs. In some embodiments, the effect is a 10%, 20%, 30%, 40%, 50%, 60%, 70% 80%, 90%, 95%, 99% or 100% reduction of survival of the CSCs. Each possibility represents a separate embodiment of the invention.

In some embodiments, metastatic potential is determined by measuring at least one of: anchorage-independent colony formation, migration, invasion, formation of metastases in a mouse. In some embodiments, the effect is a 10%, 20%, 30%, 40%, 50%, 60%, 70% 80%, 90%, 95%, 99% or 100% reduction of at least one of the measured determinants of metastatic potential.

In some embodiments, the CSCs can be used in a method for drug screening in 3D cultures. In these embodiments, proposed cancer therapeutics can be applied to a 3D culture containing CSCs. The CSCs can be any suitable CSCs obtained from a primary tumor specimen, primary tumor cultures, cancer cell lines/cell lines propagated in nude mice, or xenografts derived from any of these cultures to generate animal models. In some embodiments, the therapy of interest interacts with the CSCs to create various effects including reducing the size of the tumorsphere, decreasing mesenchymal phenotype, decreasing stemness, inducing apoptosis or inducing autophagy, inducing cell differentiation or inducing increased response to other treatments, decreasing cell migration and invasion, or combinations thereof.

In some embodiments, the CSCs express a stem cell reporter gene. Such a reporter gene, or reporter construct, is an ectopic gene operably linked to a stem cell-specific promoter. Examples of such constructs are well known in the art, and non-limiting examples include fluorescent genes such as GFP or RFP under the control of the CD44, CD133, Oct4, Sox2, or Myc promoter. Such reporters will mark only stem cells, and allow for monitoring of stemness by various assays including but not limited to microscopy or FACS. In some embodiments, the at least one effect of the therapy of interest is a negative effect on the expression of the reporter gene. In some embodiments, the effect is a 10%, 20%, 30%, 40%, 50%, 60%, 70% 80%, 90%, 95%, 99% or 100% reduction of expression of the reporter gene.

In some embodiments, the methods of the invention can be employed for the identification of tumor specific and drug-response related tumor markers. The generation of CSCs with multiple reporters of cellular and secreted luciferase and fluorescent tags allows the concomitant high throughput screening of various phenotypes, cellular responses, and signaling pathways. In some embodiments, various cellular and molecular mechanisms can be analyzed in the CSCs after application of a cancer therapeutic in order to determine positive and negative responses to different cancer therapeutics. In some embodiments, the CSCs can be used for the identification of the signaling pathways activated by the drugs, the ones that contribute to drug resistance and for analyzing cells that activate rescue mechanisms. In some embodiments, the resistant cells can be sorted and further analyzed using fluorescent reporters and tags. In some embodiments, potential treatments can be identified for relapse tumors, even before they relapse, or to be ready with a treatment if relapse does occur. Furthermore, combinations of effective cancer therapeutics can be determined by which ones affect the tumorsphere as well as the subsequent responses to therapeutics.

In some embodiments, the methods of the invention are for identifying a secondary cancer therapy, wherein said CSCs are resistant to a primary cancer therapy. In some embodiments, the present invention also provides a method of identifying rescue mechanisms in cancer cells. In some embodiments, the method comprises applying a therapy of interest to a 3D culture of CSCs, detecting changes (activation or inhibition) of a signaling pathway or changes in protein, gene, and non-coding RNA expression, and determining an appropriate cancer treatment that counteracts these changes and prevents the rescue mechanism from functioning and rendering the cells resistant to treatment. This also allows for the mechanism to be targeted in case of tumor relapse or at a stage of minimally staged disease.

In some embodiments, the methods of the invention are for providing a personalized cancer therapy to a subject in need thereof, wherein the CSCs are generated from a differentiated cancer cell from the subject or from cells with the same or similar mutations as the cancer of the subject. In some embodiments, the methods of the invention are for use in providing a personalized cancer therapy to a subject in need thereof, wherein the CSCs are generated from a differentiated cancer cell from the subject or from cells with the same or similar mutations as the cancer of the subject.

In some embodiments, the cancer cell from the subject is a primary tumor cell or a circulating tumor cell from the subject's blood, CSF or other bodily fluid. In some embodiments, a primary tumor cell from the subject in unavailable and the CSCs are generated from a cell with the same or similar mutations to the cancer of the subject. Genetic analysis of tumors is well known to one skilled in the art. In some embodiments, wherein a cancer with the same or similar mutations is not available a cancer cell of a cell line can be mutated to have the same or similar mutations. In some embodiments, similar mutations refer to, but are not limited to, mutations of proteins of the same family, and mutations that result in the same phenotype (i.e. overexpression, or silencing of a gene).

In some embodiments, tumorspheres were established from tumor cells lines from the same tumors that carry the same mutations even if not recently extracted from the subject. In some embodiments, peripheral blood can be collected from individuals to generate tumorspheres from circulating tumor cells (CTCs). In some embodiments, tumorspheres can be established from various primary cell lines which carry specific mutations and can use them as "on the shelf" cultures for drug screening for these patients. In some embodiments, the dedifferentiation of tumor cell lines into CSCs allows for the generation of "on the shelf" CSC-like cells from different tumors and with different mutations. In some embodiments, the methods of the invention are practiced on well-accepted NIH-based cell lines that are currently being used from anti-cancer drug screening.

In some embodiments, the methods of the invention further comprise analyzing expressed and secreted markers of the CSCs after application of the therapy. In some embodiments, the expressed and secreted markers that can be proteins, specific miRNAs, lncRNAs and other non-coding RNAs. In some embodiments, the expressed and secreted markers are isolated from media or exosomes or other extracellular vesicles.

In some embodiments, the expressed and secreted markers are employed for the analysis of disease presence and progression and for the response of the cells to specific treatments. In some embodiments, the analysis can be later applied for isolating circulating biomarkers from different body fluids (blood, serum, plasma, urine, CSF, saliva). In some embodiments, this method is a non-invasive procedure to analyze and predict disease progression, relapse and response to treatment.

In some embodiments, the methods of the invention further comprise, proscribing to the subject the therapy of interest as a personalized cancer therapy. In some embodiments, the methods of the invention further comprise, treating said subject by administering said therapy of interest to said subject. In some embodiments, the therapy of interest reduces survival, metastatic potential or reporter construct expression of the CSCs and is proscribed to the subject as a personalized cancer therapy. In some embodiments, the therapy of interest reduces survival, metastatic potential or reporter construct expression of the CSCs and is administered to the subject as a personalized cancer therapy.

In some embodiments, the subject has yet to have a relapse following primary cancer treatment or has had a relapse following primary cancer treatment. In some embodiments, the subject has had metastases of the cancer. In some embodiments, the subject has had a relapse following primary treatment. In some embodiments, the subject has not had a relapse following primary treatment.

In some embodiments, the present invention also provides a method of providing personalized medicine for cancer treatment screening. Therapies of interest can be applied to a 3D culture containing CSCs or tumorspheres. In some embodiments, the CSCs or tumorspheres can be obtained directly from applying the methods of the invention to cells from an individual patient's biopsy and using it in the 3D culture (spheroids, alone or with cells relevant to each tumor type, that can mimic the tumor microenvironment) in order to tailor the cancer treatment specifically to their cancer. In some embodiments, the method provides a treatment that specifically is shown to reduce the size of the tumorsphere due to inhibition of proliferation and self-renewal ability, decrease mesenchymal phenotype, decrease stemness, induce apoptosis or induce autophagy, induce cell differentiation or induce increased response to other treatments, decreasing cell migration or invasion, or combinations thereof. By observing which cancer therapeutic(s) interact with the CSCs to reduce the size of the tumorsphere due to inhibition of proliferation and self-renewal ability, decrease mesenchymal phenotype, decrease stemness, induce apoptosis or induce autophagy, induce cell differentiation or induce increased response to other treatments, decreasing cell migration or invasion, or combinations thereof. In some embodiments, the therapy is administered to an individual suffering from cancer. In some embodiments, the therapy is administered to treat the cancer and preventing metastases of the cancer. The methods of the invention can also be performed in vivo in an animal model using xenografts generated from the individual's CSCs.

There are several advantages in using CSCs in a drug screen. CSCs generate the majority of tumor cells. They maintain the genetic aberrations of the parental tumors. They can maintain a stable phenotype and genotype over a large number of propagations. They can be propagated in nude mice. They can be analyzed in vivo by generating patient derived xenografts (PDX). There is no limitation in the number of treatments that can be examined. In some embodiments, PDX can be generated using co-cultures or organoids comprising tumorspheres with amniotic MSCs or circulating MSCs from the same patients.

In some embodiments, the methods of the invention are for screening new and repurposed drugs, gene and cell therapy, and gene editing analysis. A large number of analyses can be performed in both live and non-live assays.

In some embodiments, co-cultures of relevant cell types can be analyzed and interaction cell matrix can be performed.

In some embodiments, the cancer is any type of cancer, such as, but not limited to, breast, ovary, lung, head and neck, colon, rectal, pancreatic, melanoma, brain, prostate, leukemia, sarcomas, thyroid, Non-Hodgkin Lymphoma, bladder, gliomas, endometrial, and renal cancer. In some embodiments, the cancer is a metastasis from any of these primary tumors.

In some embodiments, the present invention also provides a method of treating metastases by applying a cancer therapeutic chosen in a screen that is shown to be effective against resistant cells. In some embodiments, the effective cancer therapy should be shown in the screen to reduce the size of the tumorsphere, decrease mesenchymal phenotype, decrease stemness, induce apoptosis or induce autophagy, induce cell differentiation or induce increased response to other treatments, decreasing cell migration or invasion, or combinations thereof. Metastases may have different characteristics from the primary tumor cells and their response to different treatment may be different. In some embodiments, the CSCs or tumorspheres are generated from metastases as well as primary tumors in order to perform this method.

Cancer Vaccines

By another aspect, there is provided a method for producing a cancer vaccine, the method comprising: generating CSCs by any of the methods of the invention, incubating dendritic cells (DCs) with at least one of lysates, exosomes, or extracellular vesicles from the CSCs, and harvesting the dendritic cells, thereby producing a cancer vaccine. In some embodiments, the DCs are autologous or allogenic to a subject in need of the cancer vaccine.

As used herein, the term "vaccine" refers to a composition that improves immunity to a particular disease or activates the immune system against a particular disease. The term "cancer vaccine" as used herein refers to a composition that improves immunity to cancer, or activates the immune system again cancer cells. In some embodiments, a cancer vaccine is adapted to stimulate the immune system to attack cells of the cancer.

In some embodiments, the CSCs can be employed for the generation of tumor vaccines. CSCs can generate differentiated tumor cells and therefore can provide an infinite pool of both stem cells and differentiated tumor cells. In some embodiments, exosomes and other extracellular vesicles derived from these cells in the cultures can be employed for predicting circulating biomarkers and for generating tumor vaccines.

In some embodiments, the methods of the invention further comprise administering a composition comprising the cancer vaccine and a pharmaceutically acceptable carrier or excipient to a subject in need of a cancer vaccine. In some embodiments, administering the composition reduces the risk of developing cancer in a subject at risk for developing cancer. In some embodiments, administering the composition treats or ameliorates cancer, in a subject with cancer. In some embodiments, the risk of developing cancer is reduced by 10, 20, 30, 40, 50, 60, 70, 80, 90, 95, 99% in a subject at risk for developing cancer. Each possibility represents a separate embodiment of the invention.

The present invention also provides for a method of making a cancer vaccine, by incubating dendritic cells (DCs) (from either the subject or haploidentical to the subject) with lysates of cancer stem cells/tumorspheres, and thereby obtain a cancer vaccine. In some embodiments, the vaccines can be administered to the subject in an adjuvant setting with any suitable pharmaceutically acceptable excipients.

In some embodiments, CSC and tumorsphere-derived exosomes and other extracellular vesicles can be employed as tumor vaccines by pulsing autologous or allogeneic (haploidentical) dendritic cells (DCs) with the CSC or tumorsphere-derived exosomes and other extracellular vesicles. In some embodiments, the exosomes and other extracellular vesicles are taken-up by the DCs which induce the expression of molecules including but not limited to CD11c, MHCII and IL12 in the DCs.

Pharmaceutical Composition

As used herein, the term "carrier," or "excipient" refers to any component of a pharmaceutical composition that is not the active agent. As used herein, the term "pharmaceutically acceptable carrier" refers to non-toxic, inert solid, semi-solid liquid filler, diluent, encapsulating material, formulation auxiliary of any type, or simply a sterile aqueous medium, such as saline. Some examples of the materials that can serve as pharmaceutically acceptable carriers are sugars, such as lactose, glucose and sucrose, starches such as corn starch and potato starch, cellulose and its derivatives such as sodium carboxymethyl cellulose, ethyl cellulose and cellulose acetate; powdered tragacanth; malt, gelatin, talc; excipients such as cocoa butter and suppository waxes; oils such as peanut oil, cottonseed oil, safflower oil, sesame oil, olive oil, corn oil and soybean oil; glycols, such as propylene glycol, polyols such as glycerin, sorbitol, mannitol and polyethylene glycol; esters such as ethyl oleate and ethyl laurate, agar; buffering agents such as magnesium hydroxide and aluminum hydroxide; alginic acid; pyrogen-free water; isotonic saline, Ringer's solution; ethyl alcohol and phosphate buffer solutions, as well as other non-toxic compatible substances used in pharmaceutical formulations. Some non-limiting examples of substances which can serve as a carrier herein include sugar, starch, cellulose and its derivatives, powered tragacanth, malt, gelatin, talc, stearic acid, magnesium stearate, calcium sulfate, vegetable oils, polyols, alginic acid, pyrogen-free water, isotonic saline, phosphate buffer solutions, cocoa butter (suppository base), emulsifier as well as other non-toxic pharmaceutically compatible substances used in other pharmaceutical formulations. Wetting agents and lubricants such as sodium lauryl sulfate, as well as coloring agents, flavoring agents, excipients, stabilizers, antioxidants, and preservatives may also be present. Any non-toxic, inert, and effective carrier may be used to formulate the compositions contemplated herein. Suitable pharmaceutically acceptable carriers, excipients, and diluents in this regard are well known to those of skill in the art, such as those described in The Merck Index, Thirteenth Edition, Budavari et al., Eds., Merck & Co., Inc., Rahway, N.J. (2001); the CTFA (Cosmetic, Toiletry, and Fragrance Association) International Cosmetic Ingredient Dictionary and Handbook, Tenth Edition (2004); and the "Inactive Ingredient Guide," U.S. Food and Drug Administration (FDA) Center for Drug Evaluation and Research (CDER) Office of Management, the contents of all of which are hereby incorporated by reference in their entirety. Examples of pharmaceutically acceptable excipients, carriers and diluents useful in the present compositions include distilled water, physiological saline, Ringer's solution, dextrose solution, Hank's solution, and DMSO. These additional inactive components, as well as effective formulations and administration procedures, are well known in the art and are described in standard textbooks, such as Goodman and Gillman's: The Pharmacological Bases of Therapeutics, 8th Ed., Gilman et al. Eds. Pergamon Press (1990); Remington's Pharmaceutical Sciences, 18th Ed., Mack Publishing Co., Easton, Pa. (1990); and Remington: The Science and Practice of Pharmacy, 21st Ed., Lippincott Williams & Wilkins, Philadelphia, Pa., (2005), each of which is incorporated by reference herein in its entirety. The presently described composition may also be contained in artificially created structures such as liposomes, ISCOMS, slow-releasing particles, and other vehicles which increase the half-life of the peptides or polypeptides in serum. Liposomes include emulsions, foams, micelies, insoluble monolayers, liquid crystals, phospholipid dispersions, lamellar layers and the like. Liposomes for use with the presently described peptides are formed from standard vesicle-forming lipids which generally include neutral and negatively charged phospholipids and a sterol, such as cholesterol. The selection of lipids is generally determined by considerations such as liposome size and stability in the blood. A variety of methods are available for preparing liposomes as reviewed, for example, by Coligan, J. E. et al, Current Protocols in Protein Science, 1999, John Wiley & Sons, Inc., New York, and see also U.S. Pat. Nos. 4,235,871, 4,501,728, 4,837,028, and 5,019,369.

The carrier may comprise, in total, from about 0.1% to about 99.99999% by weight of the pharmaceutical compositions presented herein.

General methods in molecular and cellular biochemistry can be found in such standard textbooks as Molecular Cloning: A Laboratory Manual, 3rd Ed. (Sambrook et al., HaRBor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998).

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs.

It is noted that as used herein and in the appended claims, the singular forms "a," "an," and "the" include plural referents unless the context clearly dictates otherwise. Thus, for example, reference to "a polynucleotide" includes a plurality of such polynucleotides and reference to "the polypeptide" includes reference to one or more polypeptides and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272, 057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262;

3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference. Other general references are provided throughout this document.

Example 1

Generation of Cancer Stem Cells from Various Tumors

Tumor cells in nature can acquire stemness characteristics under certain conditions, among which are a process called epithelial to mesenchymal transit (EMT). Tumor cells can also be actively "de-differentiated" to stem-like cells under various conditions that will be described below.

There are various known methods to generate spheroids and allow differentiated tumor cells to acquire cancer stem cell phenotypes. Mechanical approaches include plating cells on cell repulsive substrate, culturing in continuous agitation in rotary cell culture vessel or spinner flask, and capturing in biologically inert 3D gels. In addition, there are commercial culture systems including the hanging drop methods.

Additionally, naturally occurring cancer stem cells (CSCs) can be separated and purified from tumor samples. Such cells can be propagated in culture in low adherence plates and with the addition of growth factors.

In order to generate CSCs in vitro, both primary differentiated cancer cells (primary glioma cells) as well as cells from a cancer cell line (U87 cells) were obtained. Glioma cells and U87 cells were trypsinized, and washed three times with medium +10% FCS. The cells were then resuspended in medium that was brought to a pH of 6.0 and were placed on a rotator and incubated for 45-90 minutes. The cells were then incubated in medium supplemented with EGF and FGF. The cells were optionally kept in mild hypoxic conditions (2-3% oxygen) during this second incubation and were then plated on bacterial plates.

Tumorspheres formed on these plates within one week and were removed from the cells that had attached to the dish. The tumorspheres were disaggregated and the cells were re-plated at limiting dilution to generate secondary spheroids. The secondary tumorspheres were then characterized for CSC specific markers, the ability to self-renew and the ability to generate tumors that recapitulate the parental tumors.

As can be seen in FIG. 1, cells incubated at pH-6 for 1 hour, followed by a second incubation at 3% oxygen, in DMEM/F12 media supplemented with epidermal growth factor (EGF), fibroblast growth factor (FGF) and transforming growth factor beta (TGFB) produced secondary tumor spheres with increased expression of stem cell markers Sox2, Oct4 and Klf4. Primary glioma cells from two different subjects were used, and all three groups of CSCs showed at least a 3-fold increase in expression over control untreated cells ($p<0.001$).

Figure 2:
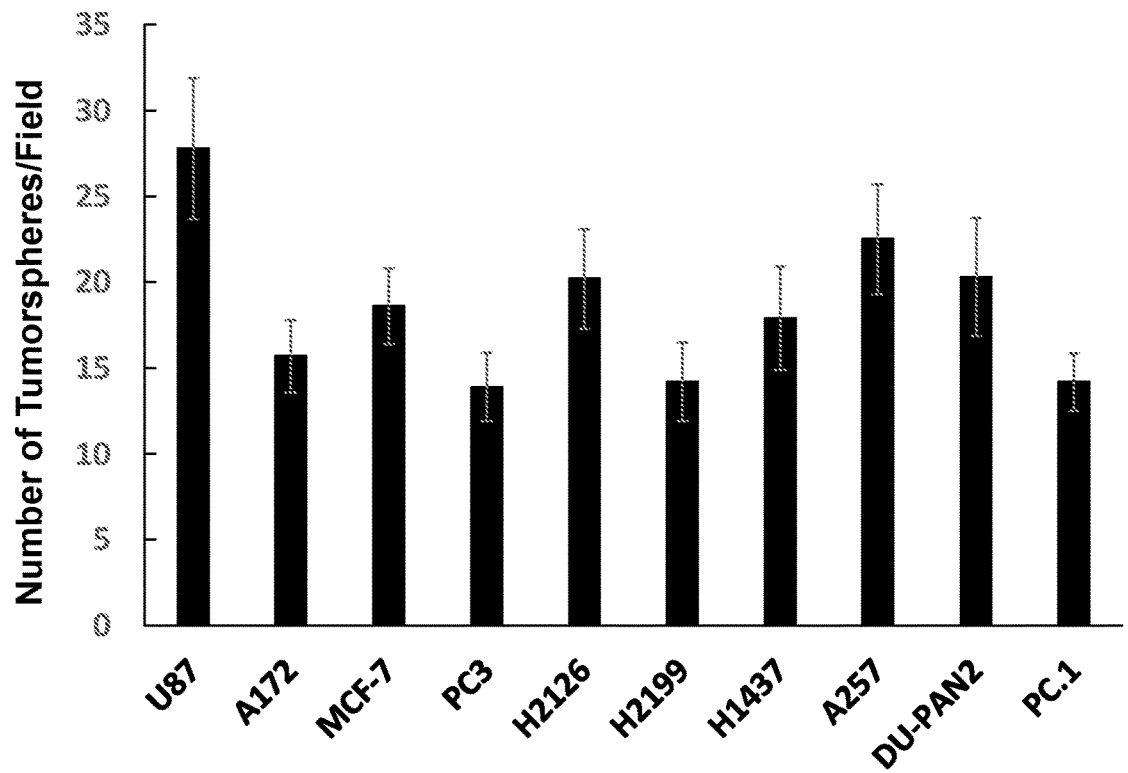
FIG. 2 is a bar graph showing the number of tumorspheres per field examined after CSC generation from various cell lines.

The same treatment was then repeated on nine other cancer cell lines. Cell lines from various tissues were used, including brain, breast, prostate, lung, and pancreases. Metastases and not metastases were used, as well as p53 positive and negative cell lines. All nice cell lines produced CSCs as evidenced by the formation of secondary tumorspheres (FIG. 2).

Example 2

Generated CSCs Can Recapitulate a Tumor in Mice

Figure 3:
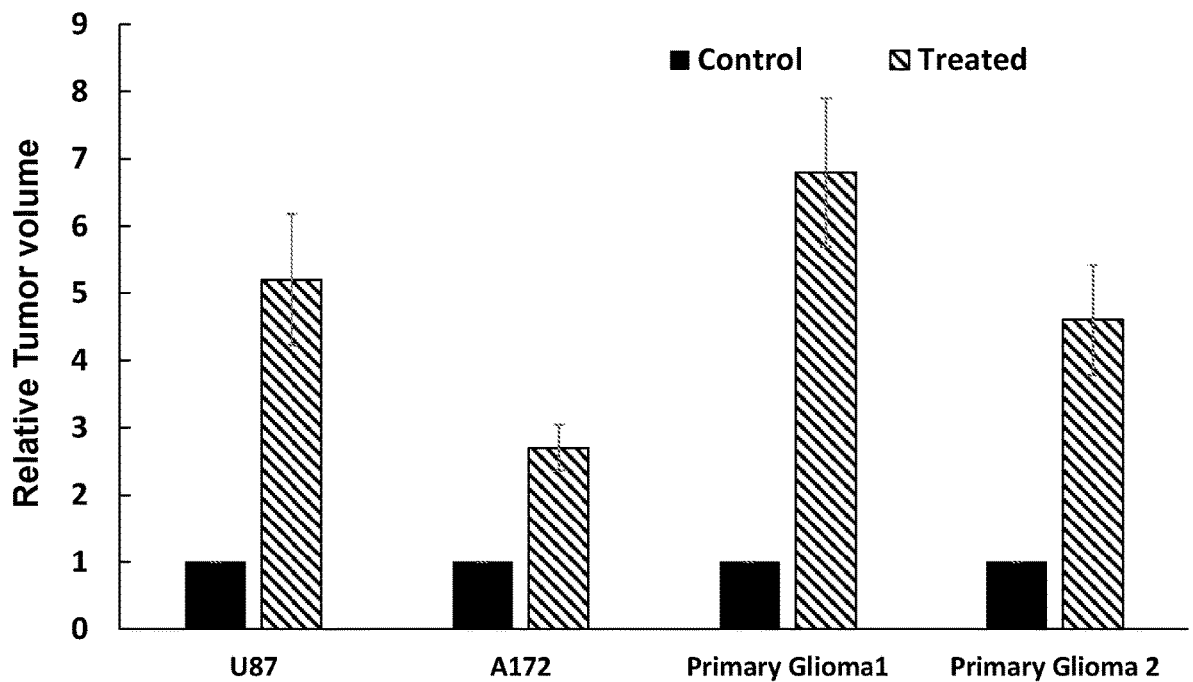
FIG. 3 is a bar graph of tumor volume for U87 cells and primary glioma cells that were dedifferentiated and injected into nude mice.

In order to determine if the newly generated CSCs could generate new tumors as naturally occur CSCs can, two glioblastoma cell lines and two samples of primary glioma cells were treated as previously described to generate CSC secondary tumorspheres. 200,000 cells from each CSC culture, as well as from non-treated cell cultures, were transplanted intracranially into nude mice. At 30 days post transplantation tumor volume was determined (FIG. 3). The results are presented, with the size of the tumor generated by each untreated sample standardized to 1. Significantly larger tumors were observed in mice that received CSCs as compared to the control cells, ($p<0.001$) with both U87 cells and one of the primary samples yielding greater than 5-fold larger tumors.

Example 3

Additional Factors for Generating CSCs: Cytokines

Knowing that the basic protocol for generating CSCs (acid, EGF/FGF and two rounds of sphere generation) was successful; several modifications to the protocol were examined. First, it was found that transfecting or transducing the cells with stem-cell reporter constructs such as GFP or RFP under the control of the CD44, CD133, Oct4, Sox2, or Myc promoters and then performing FACS sorting was useful in increasing the purity of the CSCs (data not shown). Second, a wide range of factors were found, that when supplemented to the EGF and FGF containing media, increased the efficacy of the protocol, either by increasing the number of CSCs produced or by increasing their stemness.

Figure 4A:
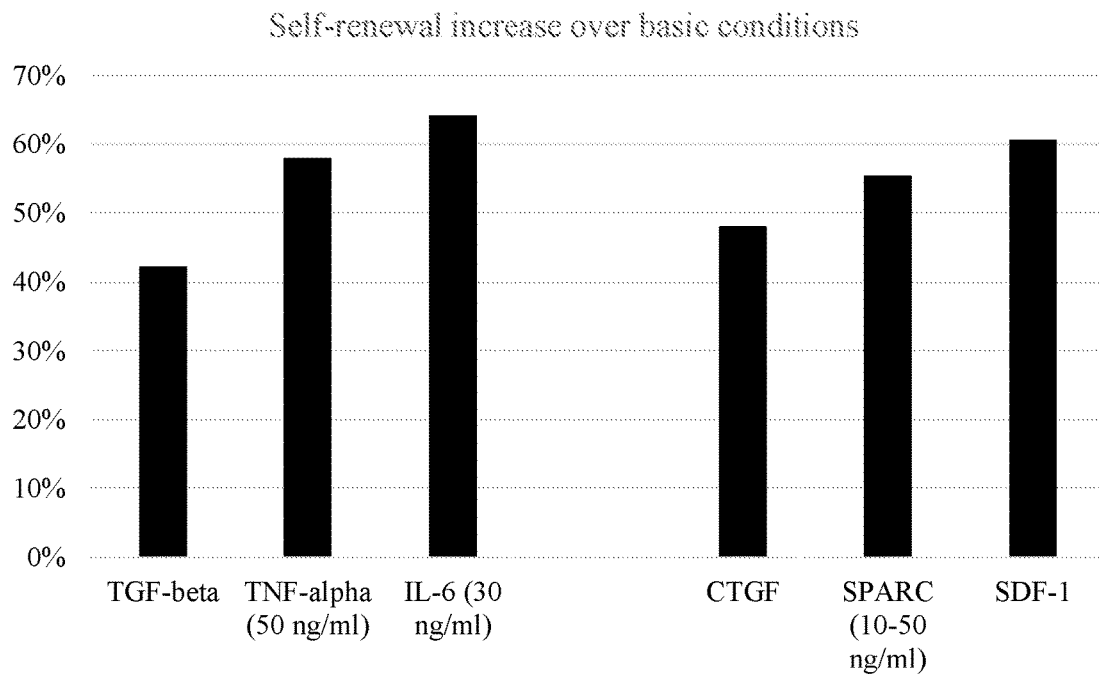
FIGS. 4A-4B. Bar graphs showing (FIG. 4A) self-renewal increase over the basic protocol and (FIG. 4B) Sox2 expression increase with addition of cytokines.
Figure 4B:
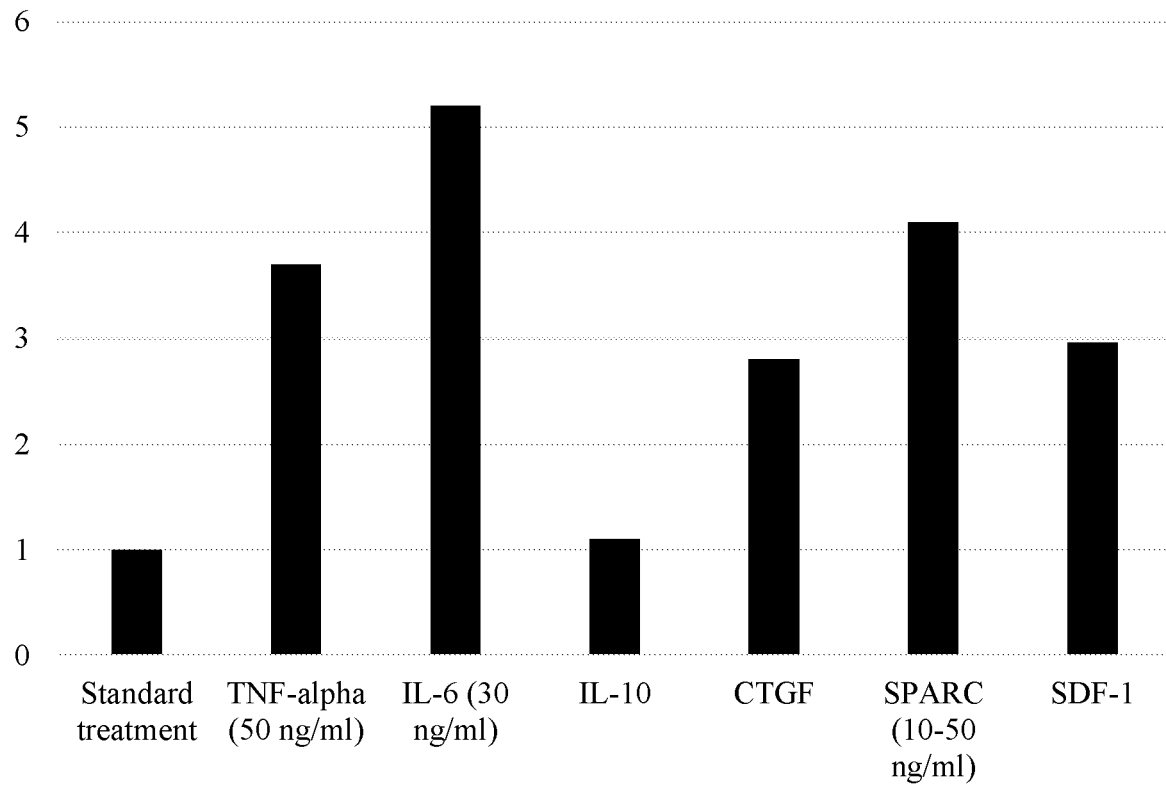

Seven different cytokines were tested as supplements to the second incubation media. Six of the seven (TGFB, TNFA, IL6, CTGF, SPARC, SDF1) increased the rate of self-renewal of the resultant CSCs as compared to the basic protocol (FIG. 4A). All six did so by at least a 40% increase. Those same six also increased the total expression of Sox2 (FIG. 4B) by at least 2-fold. IL6 was found to be most effective, as it caused a greater that 60% increase in self renewal, and a greater that 5-fold increase in Sox2 expression. In both cases, only the anti-inflammatory cytokine IL10 had no effect, although the basic protocol was still successful.

Example 4

Additional Factors for Generating CSCs: Co-Cultures

Figure 5A:
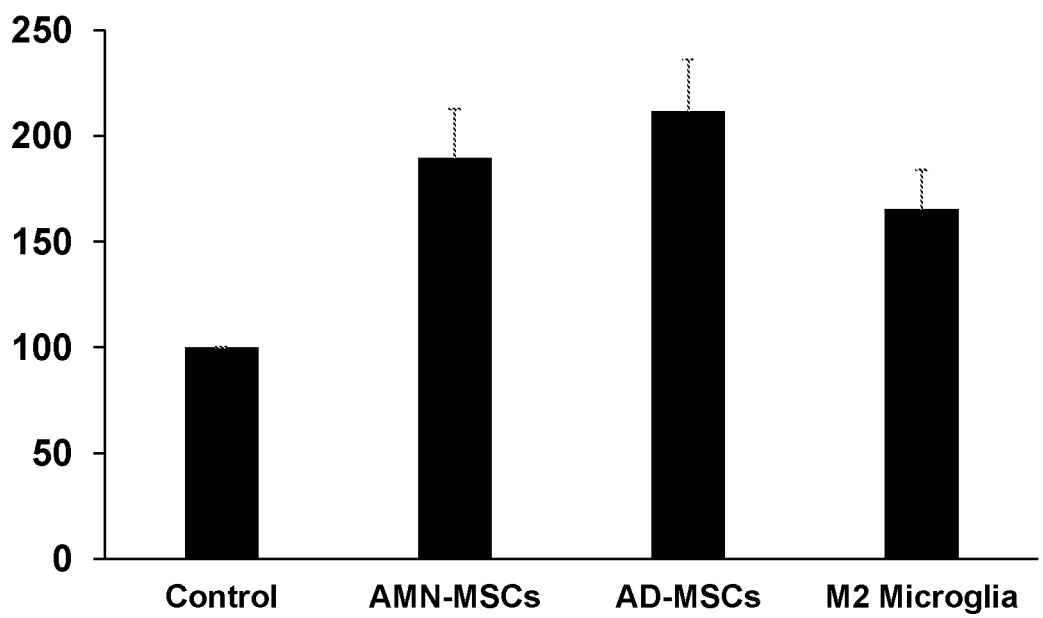
FIGS. 5A-5C. Bar graphs showing (FIG. 5A) self-renewal increase over the basic protocol and (FIG. 5B) Sox2 expression increase with co-incubation with non-cancerous cells, and expression of SOX2, OCT4, and CD44 mRNA in three glioblastoma multiform differentiated samples cultured alone, with microglia or with amniotic MSCs (FIG. 5C).
Figure 5B:
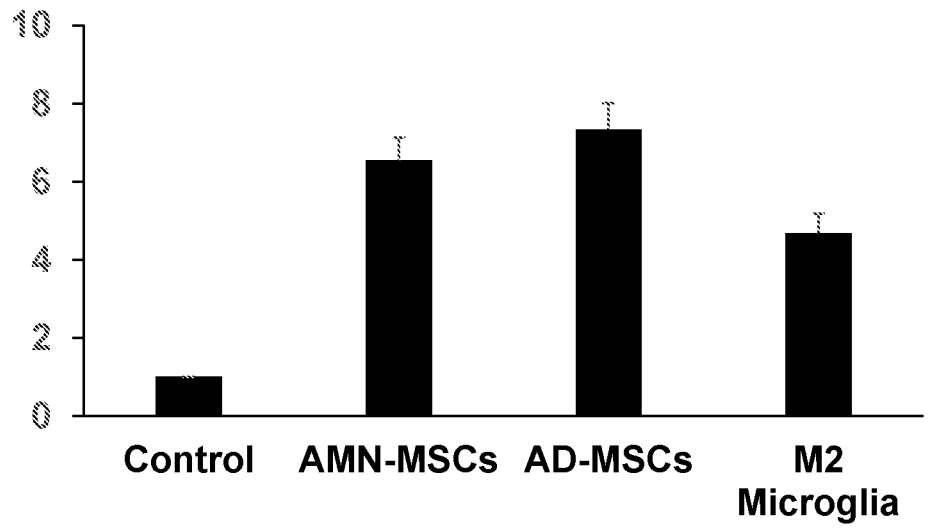

It was next tested if co-incubation with other healthy non-cancerous cells during the second incubation could improve the basic protocol. The second incubation was performed in the presence of mesenchymal stem cells (MSCs) derived from either the amnion or adipose tissue, or M2 microglia cells. All three co-incubations increased the rate of self-renewal by at least 40%, with adipose-MSCs having the strongest effect (FIG. 5A). Both MSCs and macrophages also were found to increase Sox2 expression, with co-culture with adipose-MSCs causing a nearly 7-fold increase (FIG. 5B).

Figure 5C:
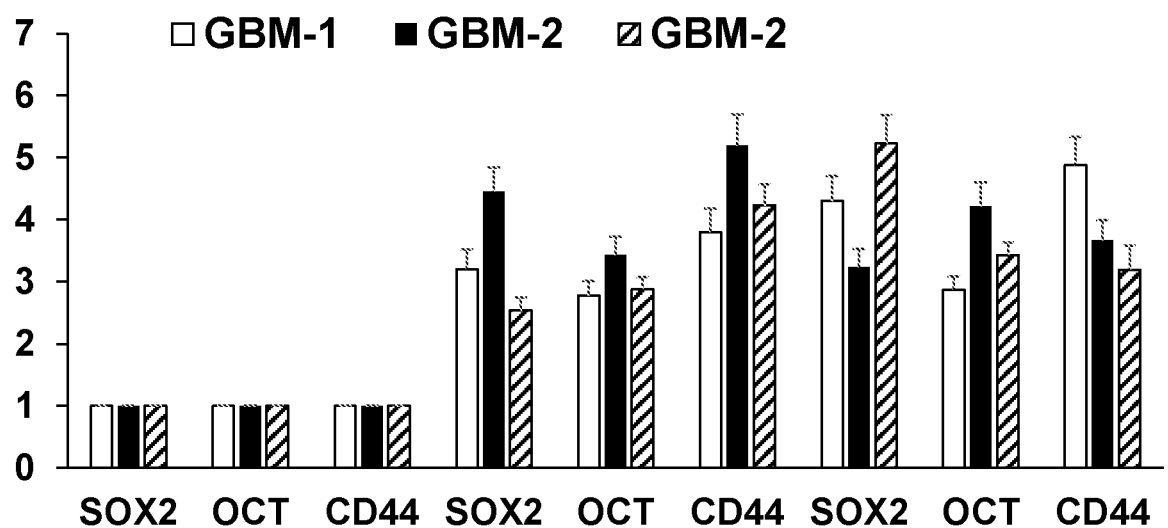

Additionally, three glioblastoma multiform differentiated samples were cultured with alone, with microglia or with amniotic MSCs. For all three samples, co-culture led to significant increases in the expression of SOX2, OCT4, and CD44 mRNA (FIG. 5C).

MSCs, macrophages and microglia cells all support the cells in their microenvironment. Additionally, all of these cells have large secretomes that effect their neighbor cells. Performing the second incubation step or growing primary or secondary tumorspheres in a transwell with 0.4-micron filter and these various supporting cells was also successful in increasing the effectiveness of the basic protocol (data not shown). This suggests that the exosomes, and other secreted factors are important in aiding dedifferentiation. Further, other stem cells were also effective when co-incubated, such as CD34+ hematopoietic progenitor cells, circulating tumor cells, tumor associated fibroblasts and MSCs autologous to the initial differentiated cancer cells.

Example 5

Additional Factors for Generating CSCs: Small Molecules

Figure 6A:
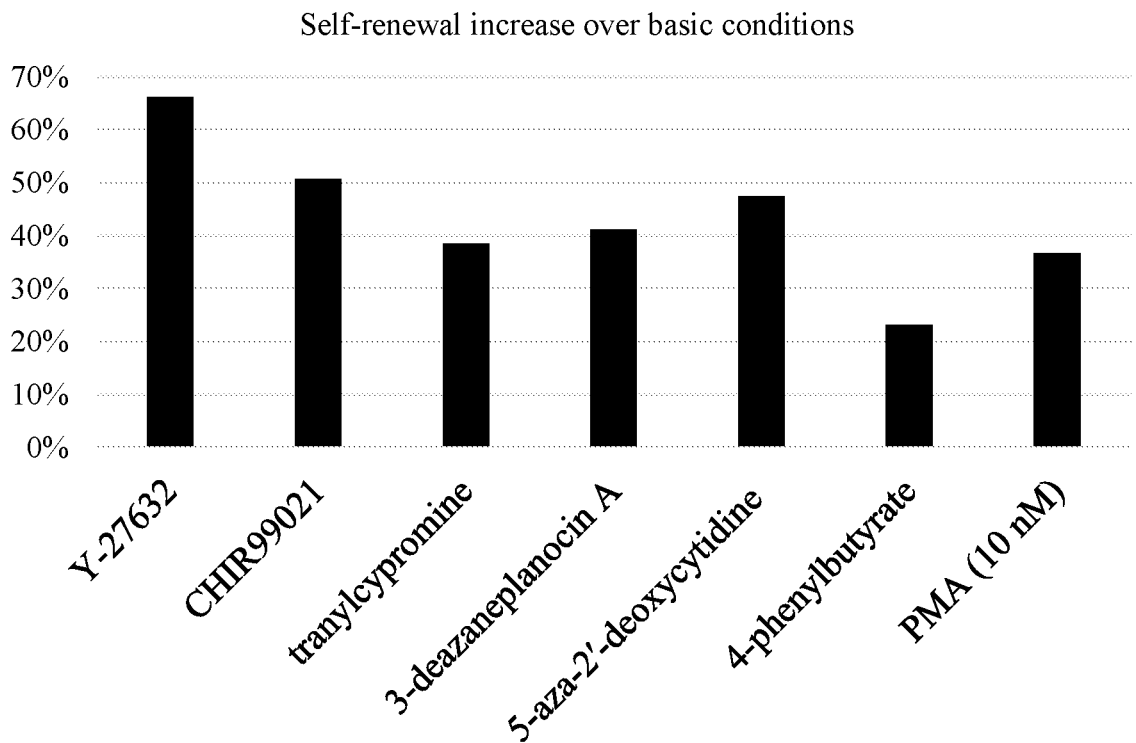
FIGS. 6A-6B. Bar graphs showing (FIG. 6A) self-renewal increase over the basic protocol and (FIG. 6B) Sox2 expression increase with addition of small molecule inhibitors and activators.

Several small molecules were added to the second incubation and their efficacy in enhancing dedifferentiation was assessed. A Rho-associated protein kinase (ROCK) inhibitor (Y-27632), a GSK3 inhibitor (CHIR99021), a monoamine oxidase inhibitor (tranylcypromine), a protein kinase C (PKC) activator (PMA), sonic hedgehog (SHH) inhibitors, ERK activators (Ceramide C6) and several histone modifying enzyme activators and inhibitors (3-deazaneplanocin A, 5-aza-2'-deoxycytidine, 4-phenylbutyrate) were tried, and all were found to increase the rate of self-renewal to varying degrees (FIG. 6A). Valporic acid, a histone deacetylase inhibitor, and insulin were also found to be effective (data not shown).

Figure 6B:
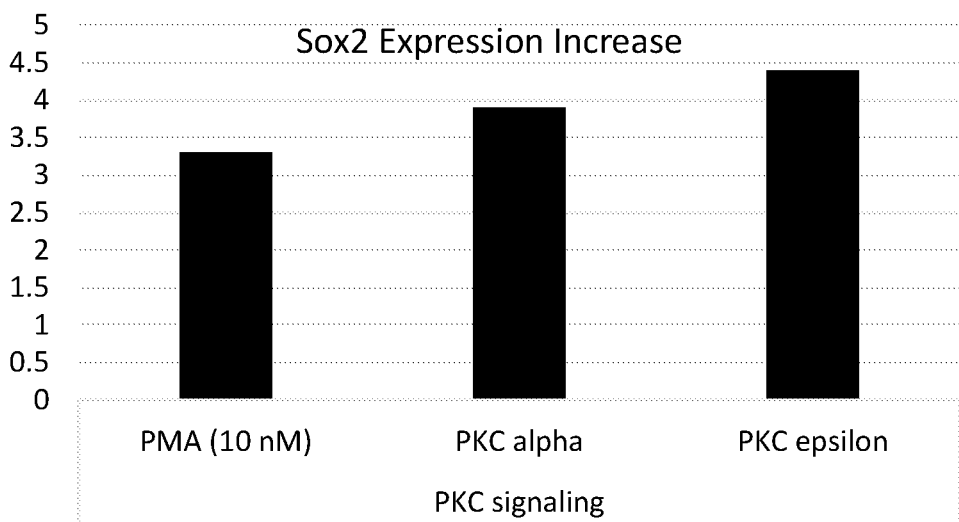

PKC activation was further investigated, and PMA, PKC alpha, and PKC epsilon were all found to increase Sox2 expression. Interestingly, both PKC alpha and PKC epsilon were both more effective that PMA (FIG. 6B).

Example 5

Additional Factors for Generating CSCs: RNAs

Figure 7A:
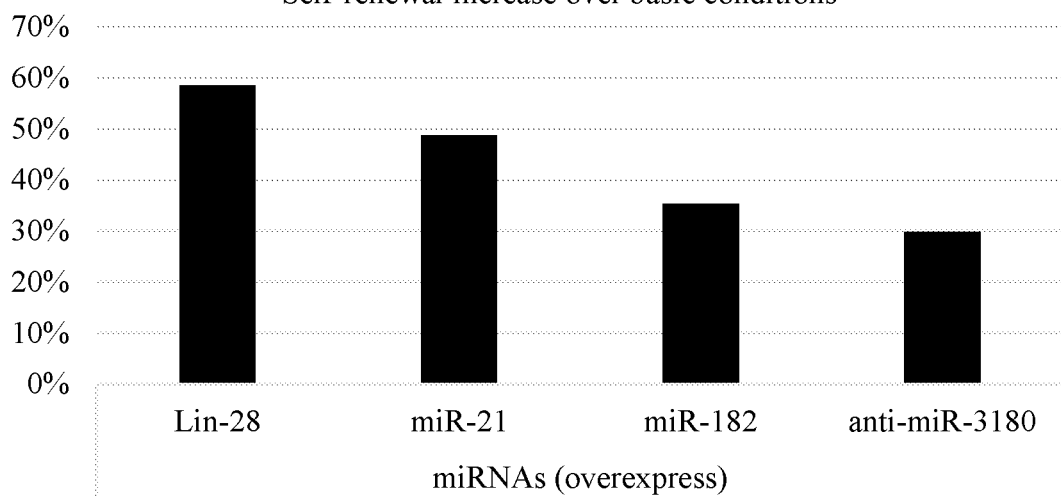
FIGS. 7A-7B. Bar graphs showing (FIG. 7A) self-renewal increase over the basic protocol and (FIG. 7B) Sox2 expression increase with addition of microRNAs and a microRNA inhibitor.
Figure 7B:
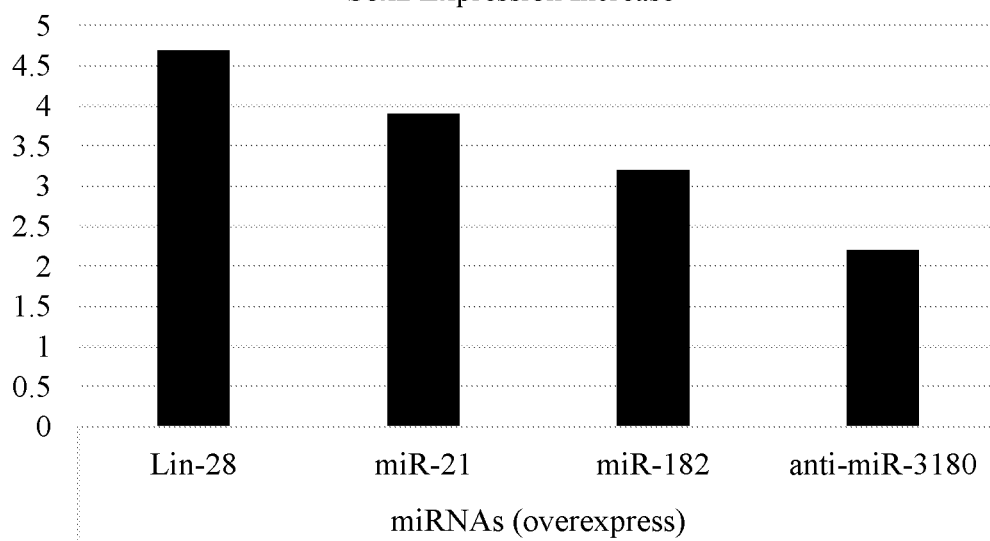

Manipulation of small interfering RNAs, such as siRNAs, shRNA and microRNAs (miRs) either by ectopic expression or expression of a polynucleotide inhibitor of those RNAs was also an effective addition to the basic protocol for creating CSCs. Ectopic or increased expression of the following miRs within the differentiated cells had a positive effect on stemness: miR-23a, miR-99b, miR-335, miR-339, miR-541, miR-3133, miR-32, miR-99b, miR-320, miR-182, miR-21, miR-138, miR-29a, miR-494, miR-335, miR-214, miR-199, miR-193, miR-196, miR-487, miR-409, miR-193, miR-379, miR-27, miR-193, miR-23, miR-24, miR-299, miR-431, and miR-154. Additionally, expression of a polynucleotide inhibitor of the following miRs within the differentiated cells also had a positive effect on stemness: miR-139, miR-831, miR-4281, miR-1268, miR-3188, miR-135, miR-1228, miR-3141, miR-1207, miR-638, miR-760, miR-2861, miR-15, miR-933, miR-3155, miR-920, miR-4310, miR-1915, miR-26b, miR-664, miR-718, miR-3176, miR-1825, miR-3180, miR-363, miR-1231, miR-20b, miR-572, miR-504, miR-30a, miR-891, miR-9, miR-874, miR-1287, miR-532, miR-362, miR-181, miR-491, miR-1208, miR-330, miR-374, miR-769, miR-501, miR-128, miR-149, miR-505, miR-660, miR-1275, 20a, miR-106, miR-636, miR-145, miR-124, miR-137. FIGS. 7A and 7B show three overexpressed miRs (Lin-28, miR-182 and miR-21) and one polynucleotide inhibitor (anti-miR-3180) that improved self-renewal (7A) and Sox2 expression (7B) over the basic protocol.

Expression of several long non-coding RNAs (lncRNAs) also had a positive effect on stemness. Expression of ZEB2NAT, UCA1, Zfhx2as, 7SL, antiPeg11, and H19 in the differentiated cells all improved the basic protocol (data not shown).

Example 6

Additional Factors for Generating CSCs: Transcription and Secreted Factors

Lastly, several transcription factors and secreted factors that are known to enhance stemness or cancer progression were introduced into the differentiated cells during the second incubation or during tumorsphere formation. Expression of STAT3, NFKB, CEBP/B, SOX2, OCT4, NANOG, WNT5A, LIF, COX2, or RUNX2 in these cells or in their media served to increase the efficacy and penetrance of the dedifferentiation brought about by the standard protocol.

Additionally, contact of the differentiated cell with SPARC, anti-CD44 antibody, RTVP1, or RTVP1b. This was performed by coating the tissue culture plates with the above listed molecules.

Example 7

3D Cultures and Organoid Generation

Experiments wherein the generated CSCs were co-incubated with healthy cells demonstrated the utility of creating more accurate 3D models of the tumor microenvironment. Such models are essentially tumor organoids, and by supporting the CSCs with MSCs, healthy cells from the tissue of origin of the CSCs, and differentiated cells of the tumor an authentic microenvironment can be created. Such organoids were especially useful for high throughput drug screening, as well as analysis of signaling pathways within the tumor and in alterations of those pathways associated with treatment.

2D, 3D cultures and organoids of non-cancerous cells were also useful drug screening models. Healthy cells, such as neuronal stem cells (NSCs), astrocytes, microglia, oligodendrocytes and differentiated neurons can be immortalized by lentiviral expression of hTERT. These cells are non-oncogenic and maintain the phenotypes and functionality of the original cells. The cells are then co-cultured with various combinations of supporting cells, including MSCs, glial cells, fibroblasts and endothelial cells. In some instances, these cells are grown in transwell plates with 0.4-micron filters that allow the transfer of soluble factors only.

These cells could further be mutated/edited so as to mimic a disease state. This was particularly useful in studying monogenetic disorders such as orphan diseases and more common neurological diseases such as Rett syndrom, familial ALS, Parkinson's disease, or any other monogenic disease. By mutating already differentiated cells in which the disease is normally manifested, the drawbacks of differentiating ESC or iPSCs from patients into mature neural cells could be circumvented. Moreover, microglia cells are very difficult to generate using ESCs or is PSCs.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

The invention claimed is:

1. A method for generating a cancer stem cell (CSC), the method comprising:
   a) providing a differentiated cancer cell,
   b) incubating said differentiated cancer cell in a first medium with a pH between 5 and 6.5,
   c) incubating said differentiated cancer cell in a second medium supplemented with epidermal growth factor (EGF) and fibroblast growth factor (FGF), optionally further comprising analyzing expressed and secreted markers of said generated CSC, thereby generating a CSC, wherein said second medium comprises a neutral pH.

2. The method of claim 1, wherein said differentiated cancer cell is selected from the group consisting of: a primary tumor cell from a subject, a cell of a cancer cell line, a circulating tumor cell from a subject's blood or lymph and a cancer cell differentiated in culture.

3. The method of claim 1, wherein said first medium has a pH between 5.8 and 6.2, optionally wherein said incubating in a first medium is performed for 15-120 minutes.

4. The method of claim 1, wherein said second medium is further supplemented with a supplement comprising at least one of
   a) at least one cytokine selected from the group consisting of: IL-6, TGF-β, TNF-α, CTGF, SPARC, and SDF1;
   b) a small molecule selected from the group consisting of: a Rho-associated protein kinase (ROCK) inhibitor, a GSK3 inhibitor, a sonic hedgehog (SHH) inhibitor, an ERK activator, a monoamine oxidase (MAO) inhibitor, a protein kinase C (PKC) activator, a histone modifying enzyme inhibitor, and a histone modifying enzyme activator; and
   c) a small molecule selected from the group consisting of: Y-27632, CHIR99021, tranylcypromine, PMA, 3-deazaneplanocin A, 5-aza-2'-deoxycytidine, 4-phenylbutyrate, PKC alpha activator, PKC epsilon activator, Ceramide C6, valproic acid and insulin.

5. The method of claim 4, wherein said second medium is further supplemented with TGF-β.

6. The method of claim 1, wherein the incubation with a second medium further comprises co-incubation with:
   a) cells selected from a group consisting of: mesenchymal stem cells (MSCs), macrophages, microglia, hematopoietic progenitors, and circulating tumor cells,
   b) cells selected from a group consisting of: amniotic MSCs, adipose MSCS, M2 macrophages, and microglia;
   c) conditioned media or exosomes from human fibroblasts, amniotic MSCs, adipose MSCs or microglia.

7. The method of claim 6, wherein the incubation with a second medium further comprises co-incubation with cells selected from the group consisting of: amniotic MSCs, adipose MSCS, M2 macrophages, and microglia, optionally wherein said MSCs are autologous to said differentiated cancer cell.

8. The method of claim 1, further comprising ectopically expressing within said differentiated cancer cell at least one of:
   a) a microRNA (miR) selected from the group consisting of: Lin-28, miR-23a, miR-99b, miR-335, miR-339, miR-541, miR-3133, miR-32, miR-99b, miR-320, miR-182, miR-21, miR-138, miR-29a, miR-494, miR-335, miR-214, miR-199, miR-193, miR-196, miR-487, miR-409, miR-193, miR-379, miR-27, miR-193, miR-23, miR-24, miR-299, miR-431, and miR-154;
   b) at least one polynucleotide inhibitor that hybridized to at least one miR selected from the group consisting of: miR-34, miR-139, miR-831, miR-4281, miR-1268, miR-3188, miR-135, miR-1228, miR-3141, miR-1207, miR-638, miR-760, miR-2861, miR-15, miR-933, miR-3155, miR-920, miR-4310, miR-1915, miR-26b, miR-664, miR-718, miR-3176, miR-1825, miR-3180, miR-363, miR-1231, miR-20b, miR-572, miR-504, miR-30a, miR-891, miR-9, miR-874, miR-1287, miR-532, miR-362, miR-181, miR-491, miR-1208, miR-330, miR-374, miR-769, miR-501, miR-128, miR-149, miR-505, miR-660, miR-1275, 20a, miR-106, miR-636, miR-145, miR-124, miR-137;
   c) a long non-coding RNA (lncRNA) selected from the group consisting of: ZEB2NAT, UCA1, Zfhx2as, 7SL, antiPeg1 1, and H19; and
   d) at least one protein selected from the group consisting of: Lin-28, STAT3, NFKB, CEBP/B, SOX2, OCT4, WNTSA, LIF, COX2, RUNX2 and NANOG.

9. The method of claim 1, further comprising irradiating said differentiated cancer cell.

10. The method of claim 1, wherein said incubating (c) in a second media further comprises incubating in a hypoxic condition, optionally wherein said hypoxic condition is 2-4% oxygen.

11. The method of claim 1, further comprising:
   d) incubating said differentiated cancer cell on non-adherent plates and selecting primary spheroids; optionally further comprising
   e) re-plating cells from said spheroids in limiting dilution to form secondary spheroids.

12. The method of claim 1, for maintaining said CSC, further comprising culturing said generated CSC with healthy cells, their exosomes, or a combination thereof, optionally wherein said healthy cells are from the same tissue of origin as said differentiated cancer cell.

13. A method for identifying an anti-cancer therapy, the method comprising:
   a) providing CSCs generated by the method of claim 1,
   b) applying a therapy of interest to said CSCs, and
   c) determining at least one effect of the therapy of interest on said CSCs, thereby identifying an anti-cancer therapy.

14. The method of claim 13, wherein said effect is a negative effect on the survival or metastatic potential of the CSCs, optionally wherein said CSCs express a stem cell reporter gene and wherein said effect is a negative effect on the expression of said reporter gene.

15. The method of claim 13, further comprising administering said CSCs to an immunodeficient mouse to generate a xenograft before applying said therapy or analyzing expressed and secreted markers of said CSCs after application of said therapy.

16. The method of claim 13, for providing a personalized cancer therapy to a subject in need thereof, wherein said CSCs are generated from a differentiated cancer cell from said subject or from cells with the same or similar mutations as the cancer of said subject, optionally wherein said cancer cell from said subject is a primary tumor cell or a circulating tumor cell from said subject's blood, CSF or other bodily fluid.

17. A method for producing a cancer vaccine, the method comprising:
   a) generating CSCs by the method of claim 1,
   b) incubating dendritic cells with at least one of lysates, exosomes or extracellular vesicles from said CSCs,
   c) harvesting said dendritic cells, thereby producing a cancer vaccine.

18. The method of claim 17, wherein said dendritic cells are autologous or allogenic to a subject in need of said cancer vaccine.

19. The method of claim 17, further comprising administering a composition comprising the cancer vaccine and a pharmaceutically acceptable carrier or excipient to a subject in need of a cancer vaccine.

20. The method of claim 1, wherein said first medium has a pH between 5.8 and 6.5, optionally wherein said incubating in a first medium is performed for 15-120 minutes.

\* \* \* \* \*